US007662750B2

(12) United States Patent
Hangauer et al.

(10) Patent No.: US 7,662,750 B2
(45) Date of Patent: Feb. 16, 2010

(54) PROTEIN-PROTEIN INTERACTION ANTAGONIST SCREENING LIBRARIES BASED UPON 1,4-DISUBSTITUTED NAPHTHALENES AND RELATED SCAFFOLDS

(75) Inventors: David G. Hangauer, East Amherst, NY (US); Tao Ji, Amherst, NY (US); Madison Lee, Buffalo, NY (US); Steven Pruitt, Williamsville, NY (US)

(73) Assignees: The Research Foundation of State University of New York, Amherst, NY (US); Roswell Park Cancer Institute, Buffalo, NY (US)

( * ) Notice: Subject to any disclaimer, the term of this patent is extended or adjusted under 35 U.S.C. 154(b) by 708 days.

(21) Appl. No.: 11/005,194

(22) Filed: Dec. 6, 2004

(65) Prior Publication Data

US 2005/0153366 A1      Jul. 14, 2005

Related U.S. Application Data

(60) Provisional application No. 60/527,102, filed on Dec. 4, 2003.

(51) Int. Cl.
*C40B 40/16*      (2006.01)
(52) U.S. Cl. .............................. 506/21; 506/13; 562/63
(58) Field of Classification Search .................. None
See application file for complete search history.

(56) References Cited

OTHER PUBLICATIONS

Dixon et al., "Preparation of a series of substituted fluoromethylnaphthalenes" Canadian Journal of Chemistry 1981, 59(17), 2629-2641.*

Buchi, J. "The Constitution-Effect Relationships from a New Viewpoint" Deutsche Apotheker-Zeitung 1966, pp. 1695-1700 (1-29 for English translation).*

Hanauska et al, 'In vitro and in vivo Predictive Tests.' In: Cancer Medicine E.5, Edited by Bast et al. London: B.C. Decker Inc. , 2000, pp. 585-588.*

Grier et al., "The Pathophysiology of HOX genes and their role in cancer" Journal of Pathology 2005, 205, pp. 154-171.*

Zhao et al., "inhibiting protein-protein interactions using designed molecules" Current Opinion in Structural Biology 2005, 15, 31-34.*

Lipinski, Annual Reports in Medicinal Chemistry, 21:283-291 (1986).*

(Continued)

*Primary Examiner*—Jeffrey S. Lundgren
(74) *Attorney, Agent, or Firm*—Nixon Peabody LLP

(57) ABSTRACT

The present invention relates to 1,4-disubstituted naphthalene scaffold compounds and other closely related scaffold compounds. The present invention also relates to combinatorial libraries of such compounds. In addition, the present invention relates to a method of identifying a protein-protein interaction antagonist. The method first involves providing a compound as described herein. Next, the compound is contacted with interacting proteins of a protein-protein interaction target complex, whereby the compound is allowed to compete with the interacting proteins. Then, the activity of the compound for inhibiting formation of the protein-protein interaction target complex is measured. Finally, the compound that inhibits formation of the protein-protein interaction target complex is identified as a protein-protein interaction antagonist. Also disclosed is a method for modulating a protein-protein interaction. The method involves contacting interacting proteins of a protein-protein interaction target with a compound as described herein, whereby the protein-protein interaction between the interacting proteins is modulated.

43 Claims, 1 Drawing Sheet

OTHER PUBLICATIONS

Patani et al., Chem. Rev., 96:3147-3176 (1996).*

Knoepfler et al., Mol. Cell. Bio., 15(10):5811-5819 (1995).*

Dixon et al., "Preparation of a Series of Substituted Fluoromethylnaphthalenes," Canadian J. of Chemistry, 59:2629-41 (1981).

Ji et al., "Privileged Scaffolds for Blocking Protein-Protein Interactions: 1,4-Disubstitued Naphthalene Antagonists of Transcription Factor Complex HOX-PBX/DNA," *Bioorganic & Medicinal Chemistry Letters* 14:3875-3879 (2004).

Knoepfler et al., "The Pentapeptide Motif of Hox Proteins is Required for Cooperative DNA Binding with Pbx1, Physically Contacts Pbx1, and Enhances DNA Binding by Pbx1," *Molecular and Cellular Biology* 15(10):5811-5819 (1995).

* cited by examiner

PROTEIN-PROTEIN INTERACTION ANTAGONIST SCREENING LIBRARIES BASED UPON 1,4-DISUBSTITUTED NAPHTHALENES AND RELATED SCAFFOLDS

This application claims the benefit of U.S. Provisional Patent Application Ser. No. 60/527,102, filed Dec. 4, 2003, which is hereby incorporated by reference in its entirety.

This invention arose out of research sponsored by the National Institute of Health (Grant No. RO1 HD 36416). The U.S. Government may have certain rights in this invention.

FIELD OF THE INVENTION

The present invention relates to 1,4-disubstituted naphthalene scaffold compounds, as well as other closely related scaffold compounds, combinatorial libraries of such compounds, methods of identifying protein-protein interaction antagonists, and methods of modulating a protein-protein interaction.

BACKGROUND OF THE INVENTION

The term "privileged structure" was first introduced by Evans et al. (Evans et al., *J. Med. Chem.* 31:2235 (1988)). The definition they provided for a privileged structure was "a single molecular framework able to provide ligands for diverse receptors." This concept was partly suggested by the finding that variously derivatized benzodiazepines have been shown to be selective ligands for a variety of proteinaceous receptor surfaces. For example, Evans et al. discovered benzodiazepine analog antagonists of the peptide hormone cholecystokinin (CCK) with binding affinities in the same range as the natural peptide ligand CCK-8 for the peripheral CCK-A receptor (Evans et al., *J. Med. Chem.* 31:2235 (1988)). Subsequent developments in benzodiazepine and other privileged structures demonstrated that derivatives of these structures can provide potent and selective agonists and antagonists for additional members of the family of G-protein coupled receptors, even though the molecular size of these non-peptide ligands are much smaller than the natural peptide ligands that they mimic (Patchett et al., *Annual Reports in Medicinal Chemistry,* 35:289, Chap. 26 (2000)). Indeed, following the discovery of benzodiazepine privileged structures, a variety of additional privileged scaffolds (i.e. the substructures upon which the privileged structures are based) have been reported (Horton et al., *Chemical Reviews* 103(3):893 (2003)). Examples include biphenyl, diphenylmethane, benzopyran (Nicolaou et al., *J. Am. Chem. Soc.* 122:9939 (2000)), indole, and benzylpiperidine, among others (Horton et al., *Chemical Reviews* 103(3):893 (2003)). Focused combinatorial libraries based upon these privileged scaffolds have typically provided enriched "hit rates" of receptor agonists/antagonists, ion channels modulators, or enzyme inhibitors, when suitably decorated with appropriate side chains to impart both potency and selectivity.

The privileged structure concept suggests that the intersection of biological diversity space and chemical diversity space tends to occur in particular "nodes" and that privileged scaffolds are positioned within the chemical diversity space of these intersection nodes. This is the underlying concept for "gene-family" screening libraries (e.g. PCT International Publication No. WO 03/19183 to Grootenhuis et al.). From a molecular viewpoint, one can understand this concept in that nature, through the process of divergent evolution, tends to conserve protein molecular features that do not need to be changed and focuses on modifying particular features that are under evolutionary pressure to change in order to take on a new function (Murzin, *Current Opinion in Structural Biology* 8:380 (1998)). This is a much more efficient evolutionary process than attempting to de novo evolve a new protein for each new needed function. Consequently, one would expect that, within a evolutionarily related gene lineage, there will be certain general structural features within binding cavities that are conserved, whereas the finer details of the topology of these binding cavities will differ to reflect the particular specificities of each individual gene family member. The approximate size and shape of evolutionarily related binding cavities are the properties that would be expected to be conserved, whereas the particular amino acids lining the cavity and the exact position and size of resulting indentations or protrusions in the cavity are the features that would expect to be altered in individual proteins.

With this background in mind, one can envision how privileged scaffolds can be "designed" rather than relying on an empirical discovery, as has typically been the case in the past. The most efficient design approach would be to start with the X-ray or nuclear magnetic resonance (NMR) structure for a representative member of the evolutionarily related proteins. One can then utilize the range of molecular modeling technologies that are currently available to evaluate various candidate scaffolds for their ability to fit in the "middle" of the binding cavity and still allow space for the positioning of various appended side chains for favorable interactions with the amino acids that line the binding cavity. This central positioning of the privileged scaffold also provides a buffer zone around the scaffold, wherein the evolutionarily related proteins can display indentations and protrusions that can interdigitate with the side chains appended to the scaffold without interfering with the ability of the scaffold to bind in the cavity. The presence, nature, and positioning of the appended side chains on these scaffolds will then determine the specificity of the individual compounds due to their ability to interact with the amino acids forming the indentations and protrusions on the cavity surface. One can then synthesize probe libraries around each in silico identified privileged scaffold to determine experimentally which scaffolds are effective.

Designing screening libraries for identifying protein-protein interaction antagonists and, indeed, discovering protein-protein interaction antagonists in general have become a major challenge in drug discovery for the post-genomic era, due to the enormous number of potential untapped drug targets within this category. The ability of proteins to selectively bind to each other forms the foundation of much of biology, including disease biology. Cell architecture, signal transduction, and gene transcription are examples of important cell processes that are at least partly controlled by carefully scripted protein-protein interactions, and are processes that can lead to disease when abnormally altered. Many protein-protein "homodimers" bind very tightly through large, hydrophobic, surfaces, and their monomeric proteins are often unstable due to ready denaturization. In contrast, protein-protein "heterodimers" often bind less tightly, and their contact surfaces are typically more hydrophilic than those of homodimers. Consequently, these proteins tend to be stably folded as monomers and exist in equilibrium with their respective protein complexes. Protein-protein heterodimers are therefore generally considered more amenable targets for small molecule antagonists, because the equilibrium between free monomer and protein complex is more readily disrupted. This equilibrium can be altered by binding to one of the protein partners at the interaction interface, or through an allosteric site. Blocking a heterodimer complex that supports a particular disease biology may not necessarily require that the formation of heterodimer be completely inhibited; rather shifting the equilibrium may be sufficient. Discovering antagonists of protein-protein interactions is widely recognized as much more challenging than discovering enzyme inhibitors or receptor antagonists, even though these drug targets often involve protein substrates or ligands, respectively. The challenges and potential of this field, as well as progress to date, are summarized in several review articles, such as Gadek et al., *Biochemical Pharmacology* 65:1 (2003), Toogood, *J. Med. Chem.* 45(8):1543 (2002), and Cochran, *Chemistry & Biology* 7(4): R85 (2000). Gadek et al. pointed out that " . . . as recently as 5 years ago the existence of small molecule antagonists was controversial. However, the antagonism of protein-protein interactions by small molecules is now well recognized, and the issue focuses on how these antagonists may be efficiently identified" (Gadek et al., *Biochemical Pharmacology* 65:1 (2003)).

Most protein-protein antagonists have been discovered by random screening rather than by design, and when the generally accepted MW 500 limit for compounds that are likely to be orally active drugs is applied to the reported antagonists, the majority have potencies in the 1-100 µM range (Boger et al., *Angew. Chem. Int. Ed.* 42:4138 (2003)). The results reported to date demonstrate that obtaining high potency, while maintaining a low molecular weight, is particularly challenging for these drug targets as compared to the more traditional drug targets. The maximum binding affinity possible for a small molecule to a particular protein-protein interaction target will depend upon the nature of the binding interface of the two proteins. Although protein-protein interactions typically involve a large surface area of contact, i.e. greater than 600 $Å^2$, most of the binding affinity is derived from "hot spots" located near the center of the contact surface (Bogan et al., *J. Mol. Biol.* 280:1 (1998)). In many cases, these hot spots are not deep cavities in the protein surface, in contrast to the deep crevice binding cavities typical for enzyme inhibitors/substrates. A detailed analysis of protein-protein interactions surfaces indicated that the binding affinity attributed to these hot spots is increased by the exclusion of water from this region of the interface by a surrounding hydrophobic "O-ring" of residues (Bogan et al., *J. Mol. Biol.* 280:1 (1998)). The exclusion of water by the hydrophobic O-ring was proposed to strengthen the interactions in the hot spots by decreasing the dielectric of the microenvironment, thereby strengthening polar interactions, and by reducing the rate of dissociation between hydrophobic groups. Consequently, binding affinity for small molecule protein-protein antagonists may be derived from two factors: 1) the shape and electronic surface complementarity of the small molecule for the hot spot, and 2) the ability of the small molecule to also shield key interactions from bulk solvent. The deeper the binding cavity forming a hot spot the more traditional binding affinity factors will be involved. The more open the binding cavity the more solvent shielding may be important.

The factors described above result in a much higher level of challenge for rationally designing tight binding, low molecular weight, antagonists of protein-protein interactions, as compared to the traditional drug targets.

Experience to date has shown that random high-throughput screening for antagonists of protein-protein interactions has generally been much less successful than has similar screening for other drug targets such as receptor antagonists, enzyme inhibitors or ion channel blockers. This may be due to using screening libraries not suitably biased towards small molecules that have the needed topology for binding to the target protein surface. In order to appreciate the scale of the problem, one needs to recognize that the volume of oral drug-sized chemical diversity space (i.e. MW ca. 500 or less) is enormous. Estimates have put the number of possible compounds with molecular weights of 500 Da or less at $10^{200}$ compounds. Even when the typical filters for selecting only drug-sized molecules that are also expected to have drug-like properties (beyond MW) are applied, this number only reduces to $10^{60}$ compounds (see Horton et al., *Chemical Reviews* 103(3):893 (2003)). As Horton et al. points out, "the proportion of these drug-like molecules synthesized to date has been estimated as one part in $10^{57}$, or roughly the ratio of the mass of one proton to the mass of the sun" (Horton et al., *Chemical Reviews* 103(3):893 (2003)). Clearly, there is a pressing need to develop better methods for "targeting" the region of chemical diversity space wherein drug-like antagonists of "drugable" protein-protein interactions reside. It is impossible to cover the total volume of drug-like chemical diversity space with any reasonable density by random broad screening. Toogood, *J. Med. Chem.* 45(8):1543 (2002) states that "currently, there are no general techniques or approaches that will reliably illuminate the path toward the synthesis of potent and effective drug-like protein-protein binding inhibitors." Toogood then goes on to state "it is hoped that over time some themes may emerge, highlighting for example particular generic structures that may form a basis for protein-protein binding inhibitors. Compound libraries then can be populated with compounds exemplifying these structures, increasing the chances of lead discovery through high throughput screening. Perhaps then the trepidation that protein-protein binding currently imbues in many medicinal chemists will be overcome, and the rich opportunities available for drug discovery finally will be recognized" (Toogood, *J. Med. Chem.* 45(8):1543 (2002)).

Transcription factor complexes are responsible for much of the regulation of gene expression (Wolgerger, *Ann. Rev. Biophys. Biomol. Struct.* 28:29 (1999)) and therefore offer many potential protein-protein interaction drug targets (Emery et al., *Trends in Pharmacological Sciences,* 22:233 (2001)), including anti-cancer targets (Karamouzis et al., *Clinical Cancer Research* 8:949 (2002)). The 39 members of the HOX family (Scott, *Cell.* 71:551 (1992)) and 4 members of the PBX family (Knoepfler et al., *Mech. Dev.* 63:5 (1997)) are proteins that bind DNA as heterodimers to form transcription factor complexes. The numerous heterodimeric HOX/PBX combinations play critical and complex roles in transcriptional regulation during patterning in early embryonic development (Knoepfler et al., *Mech. Dev.* 63:5 (1997)) and many are utilized again in specific tissues of the adult (van Oostveen et al., *Leukemia* 13:1675 (1999)). A variety of cancers display altered HOX gene regulation (Maroulakou et al., *Anticancer Research* 23:2101 (2003)). For example, in leukemias and lung cancers, HOX genes are overexpressed and consequently antagonists of the HOX/PBX complexes controlling these genes offers the potential for novel anticancer drugs. Also, small molecule antagonists of individual (or subsets) HOX/PBX complexes can be used as pharmacological tools to investigation their function.

It would be advantageous to find small molecule antagonists of protein-protein interactions, such as HOX-PBX protein-protein interactions.

The present invention is directed to achieving this objective.

SUMMARY OF THE INVENTION

The present invention relates to combinatorial libraries of compounds as described below.

Another aspect of the present invention relates to a compound having the following formula:

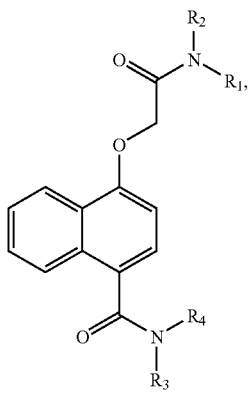

Formula I

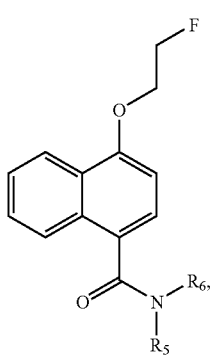

Formula II

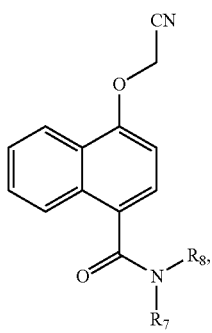

Formula III

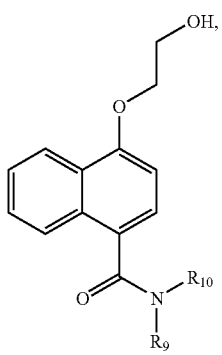

Formula IV

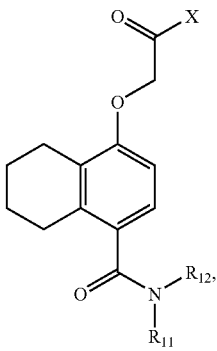

Formula V

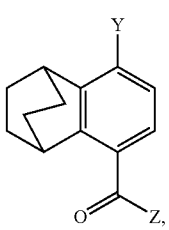

Formula VI

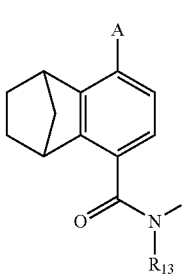

Formula VII where:

$R_1$-$R_{14}$ are individually selected from the group consisting of: H, $C_1$-$C_{12}$ alkyl, heteroatom and multiple heteroatom substituted $C_1$-$C_{12}$ alkyl, $C_1$-$C_{12}$ branched or cyclic alkyl, heteroatom and multiple heteroatom substituted $C_1$-$C_{12}$ branched or cyclic alkyl aryl and substituted aryl, heteroaryl and substituted heteroaryl, alkylaryl and substituted alkylaryl, wherein the substitution includes a heteroatom substitution in the alkyl and/or aryl group, alkylheteroaryl and substituted alkylheteroaryl, amines, $CH_2COOCH_2CH_3$, $CH_2COOH$, and $(CH_2CH_2)_2O$;

$R_1$-$R_{14}$ can optionally be side chains with one or more halogen atoms and functional groups selected from the group consisting of: amides, ureas, ketones, sulfonamides, phosphoramides, alcohols, thiols, esters, amines, amidines, guanidines, carboxylic acids, sulfonic acids, phosphonic acids, boronic acids, hydrophilic substituents, and hydrophobic substituents, wherein the functional group can be further substituted with one or more ring heteroatoms or one or more halogens;

X, Y, Z, and A are individually selected from the group consisting of: H, $C_1$-$C_{12}$ alkyl, heteroatom and multiple heteroatom substituted $C_1$-$C_{12}$ alkyl $C_1$-$C_{12}$ branched or cyclic alkyl heteroatom and multiple heteroatom substituted $C_1$-$C_{12}$ branched or cyclic alkyl, aryl and substituted aryl, heteroaryl and substituted heteroaryl, alkylaryl and substituted alkylaryl, wherein the substitution includes a heteroatom substitution in the alkyl and/or aryl group, alkylheteroaryl and substituted alkylheteroaryl, amines, CH$_2$COOCH$_2$CH$_3$, CH$_2$COOH, and (CH$_2$CH$_2$)$_2$O;

X, Y, Z, and A can optionally be side chains with N, S, O P, or B substituted with any combination of H, C$_1$-C$_{12}$ alkyl, heteroatom and multiple heteroatom substituted C$_1$-C$_{12}$ alkyl C$_1$-C$_{12}$ branched or cyclic alkyl, heteroatom and multiple heteroatom substituted C$_1$-C$_{12}$ branched or cyclic alkyl aryl and substituted aryl, heteroaryl and substituted heteroaryl, alkylaryl and substituted alkylaryl, and alkylheteroaryl and substituted alkylheteroaryl, wherein the N, S, or O can also be further attached to a carbonyl, sulfonyl, sulfinyl, or phosphoryl group to form a functional group selected from the group consisting of urea, amide, urethane, sulfonamides sulfinamide, sulfonylurea, sulfinylurea, and phosphoramides ketone, alcohol, thiol, ester, amine, amidine, guanidine, carboxylic acid, sulfonic acid, phosphonic acid, and boronic acid, wherein the functional group can be further substituted with H, C$_1$-C$_{12}$ alkyl heteroatom and multiple heteroatom substituted C$_1$-C$_{12}$ alkyl, C$_1$-C$_{12}$ branched or cyclic alkyl, heteroatom and multiple heteroatom substituted C$_1$-C$_{12}$ branched or cyclic alkyl aryl and substituted aryl, heteroaryl and substituted heteroaryl, alkylaryl and substituted alkylaryl, or alkylheteroaryl and substituted alkylheteroaryl, wherein all of the side chains with N, S, O, P, or B can optionally contain one or more halogen atoms and a functional group selected from the group consisting of amide, urea, ketone, sulfonamide, phosphoramide, alcohol, thiol, ester, amine, amidine, guanidine, carboxylic acid, sulfonic acid, phosphonic acid, and boronic acid, or a pharmaceutically acceptable salt thereof.

The present invention also relates to a method of identifying a protein-protein interaction antagonist. The method first involves providing a compound as described above. Next, the compound is contacted with interacting proteins of a protein-protein interaction target complex, whereby the compound is allowed to compete with the interacting proteins. Then, the activity of the compound for inhibiting formation of the protein-protein interaction target complex is measured. Finally, the compound that inhibits formation of the protein-protein interaction target complex is identified as a protein-protein interaction antagonist.

Another aspect of the present invention relates to a method for modulating a protein-protein interaction. The method involves contacting interacting proteins of a protein-protein interaction target with a compound as described above, whereby the protein-protein interaction between the interacting proteins is modulated.

The present invention addresses the challenge of developing "generic structures" or "privileged scaffolds" for the construction of screening libraries targeted for particular types of protein-protein interactions. Once a suite of these privileged scaffolds becomes available and are linked to particular types of protein-protein interactions for which they have demonstrated utility, these scaffolds can be used by combinatorial medicinal chemists for the generation of large protein-protein interaction antagonist screening libraries. The process of successfully developing these privileged scaffolds also provides a template upon which additional privileged scaffold development efforts can be modeled.

The present invention discloses small molecule antagonists of HOX-PBX protein-protein interactions. Structure-based-design studies, with the crystal structure of the HOXB1-PBX1/DNA transcription factor complex, were used to identify 1,4-disubstituted naphthalenes as potential antagonists. An initial library of 32 analogs was synthesized, two of which were found to be more potent than the reported activity for a 12 amino acid peptide antagonist. Antagonists were also identified of the related BRN1/DNA and BRN2/DNA transcription factor complexes indicating that a 1,4-disubsituted naphthalene may be a privileged scaffold for preparing screening libraries targeting this family of transcription factor complexes.

DETAILED DESCRIPTION OF THE INVENTION

Figure 1:
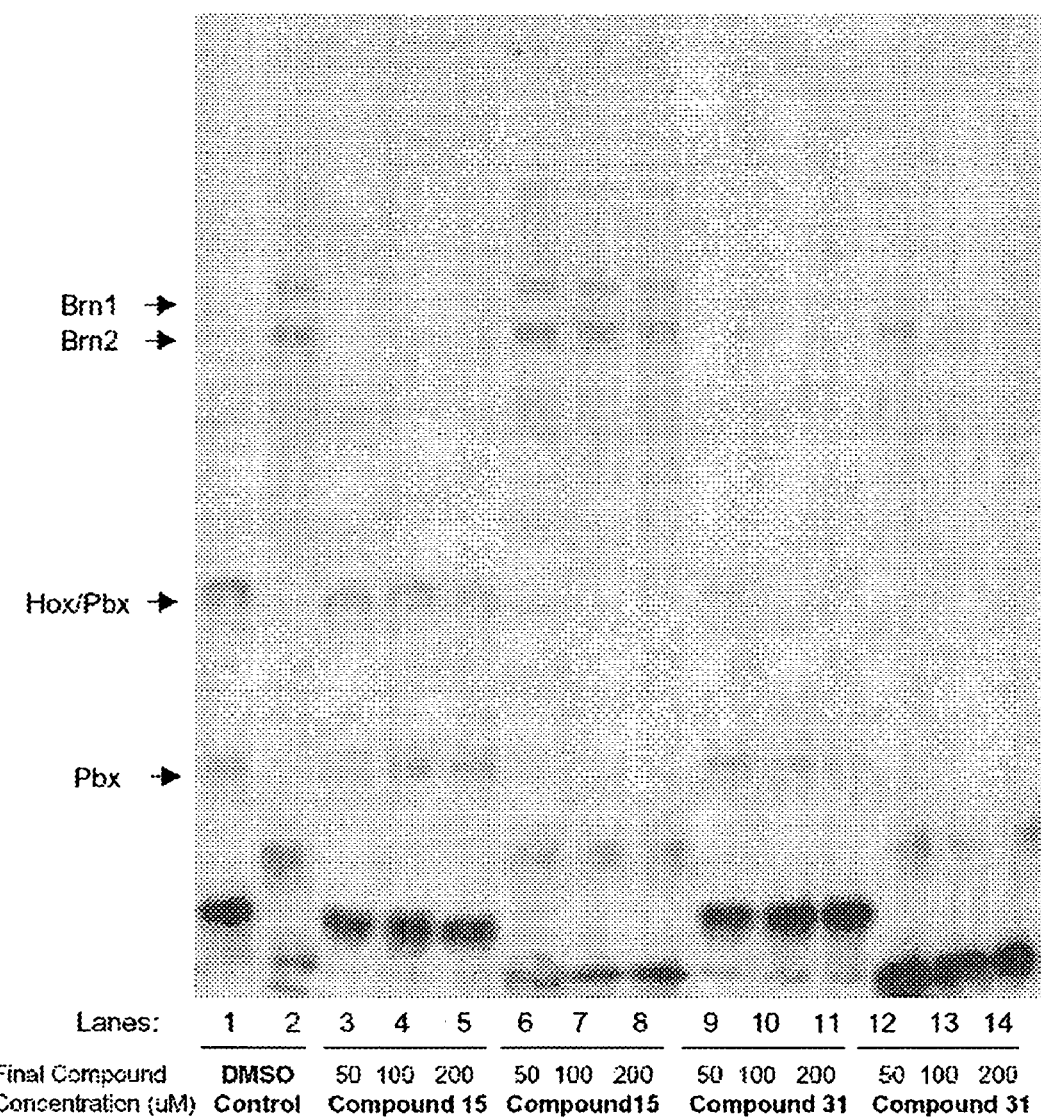
FIG. 1 illustrates the selectivity of compounds 15 and 31 for HOXA1-PBX1/DNA, PBX1/DNA, BRN1/DNA and BRN2/DNA.

The present invention relates to a combinatorial library including two or more compounds having the following formula:

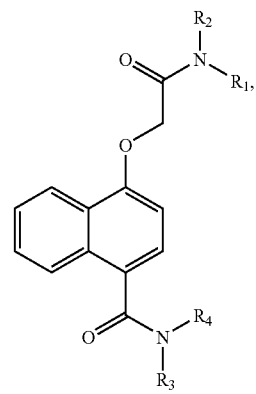

Formula I

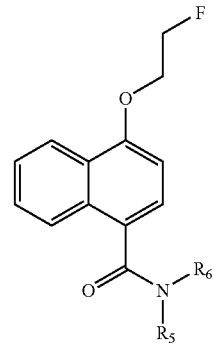

Formula II

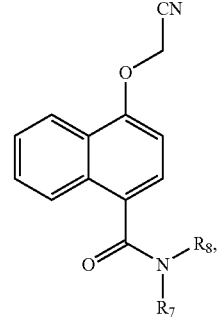

Formula III

-continued

Formula IV

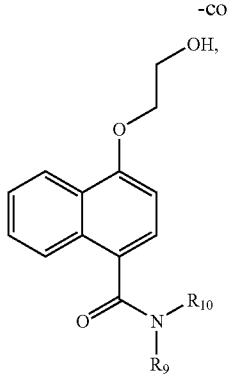

Formula V

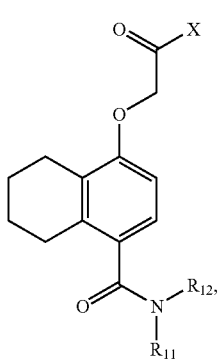

Formula VI

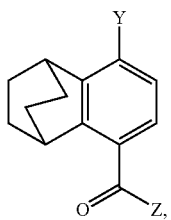

Formula VII

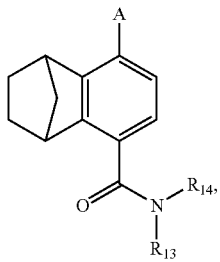

where:

$R_1$-$R_{14}$ are individually selected from the group consisting of: H, $C_1$-$C_{12}$ alkyl, heteroatom and multiple heteroatom substituted $C_1$-$C_{12}$ alkyl, $C_1$-$C_{12}$ branched or cyclic alkyl, heteroatom and multiple heteroatom substituted $C_1$-$C_{12}$ branched or cyclic alkyl, aryl and substituted aryl, heteroaryl and substituted heteroaryl, alkylaryl and substituted alkylaryl, wherein the substitution includes a heteroatom substitution in the alkyl and/or aryl group, alkylheteroaryl and substituted alkylheteroaryl, amines, $CH_2COOCH_2CH_3$, $CH_2COOH$, and $(CH_2CH_2)_2O$;

$R_1$-$R_{14}$ can optionally be side chains with one or more halogen atoms and functional groups selected from the group consisting of amides, ureas, ketones, sulfonamides, phosphoramides, alcohols, thiols, esters, amines, amidines, guanidines, carboxylic acids, sulfonic acids, phosphonic acids, boronic acids, hydrophilic substituents, and hydrophobic substituents, wherein the functional group can be further substituted with one or more ring heteroatoms or one or more halogens;

X, Y, Z, and A are individually selected from the group consisting of: H, $C_1$-$C_{12}$ alkyl, heteroatom and multiple heteroatom substituted $C_1$-$C_{12}$ alkyl, $C_1$-$C_{12}$ branched or cyclic alkyl, heteroatom and multiple heteroatom substituted $C_1$-$C_{12}$ branched or cyclic alkyl, aryl and substituted aryl, heteroaryl and substituted heteroaryl, alkylaryl and substituted alkylaryl, wherein the substitution includes a heteroatom substitution in the alkyl and/or aryl group, alkylheteroaryl and substituted alkylheteroaryl, amines, $CH_2COOCH_2CH_3$, $CH_2COOH$, and $(CH_2CH_2)_2O$;

X, Y, Z, and A can optionally be side chains with N, S, O, P, or B substituted with any combination of H, $C_1$-$C_{12}$ alkyl, heteroatom and multiple heteroatom substituted $C_1$-$C_{12}$ alkyl, $C_1$-$C_{12}$ branched or cyclic alkyl, heteroatom and multiple heteroatom substituted $C_1$-$C_{12}$ branched or cyclic alkyl aryl and substituted aryl, heteroaryl and substituted heteroaryl, alkylaryl and substituted alkylaryl, and alkylheteroaryl and substituted alkylheteroaryl, wherein the N, S, or O can also be further attached to a carbonyl, sulfonyl, sulfinyl, or phosphoryl group to form a functional group selected from the group consisting of urea, amide, urethane, sulfonamides sulfinamide, sulfonylurea, sulfinylurea, and phosphoramides ketone, alcohol, thiol, ester, amine, amidine, guanidine, carboxylic acid, sulfonic acid, phosphonic acid, and boronic acid, wherein the functional group can be further substituted with H, $C_1$-$C_{12}$ alkyl heteroatom and multiple heteroatom substituted $C_1$-$C_{12}$ alkyl, $C_1$-$C_{12}$ branched or cyclic alkyl, heteroatom and multiple heteroatom substituted $C_1$-$C_{12}$ branched or cyclic alkyl, aryl and substituted aryl, heteroaryl and substituted heteroaryl, alkylaryl and substituted alkylaryl, or alkylheteroaryl and substituted alkylheteroaryl, wherein all of the side chains with N, S, O, P, or B can optionally contain one or more halogen atoms and a functional group selected from the group consisting of amide, urea, ketone, sulfonamide, phosphoramide, alcohol, thiol, ester, amine, amidine, guanidine, carboxylic acid, sulfonic acid, phosphonic acid, and boronic acid.

As used herein, the term alkyl refers to a saturated aliphatic hydrocarbon including straight chain and branched chain groups. The alkyl group may be substituted or unsubstituted. Suitable substituents include, but are not limited to, cycloalkyl, aryl, heteroaryl, heteroalicyclic, hydroxy, alkoxy, aryloxy, thiohydroxy, thioalkoxy, thioaryloxy, cyano, halogen, carbonyl, thiocarbonyl, carboxy, nitro, silyl, and amino. A cyclic alkyl group refers to an all carbon monocyclic or fused ring (i.e., rings which share an adjacent pair of atoms) group wherein one or more of the rings does not have a completely conjugated pi-electron system. Suitable cyclic alkyl groups include, but are not limited to, cyclopropane, cyclobutane, cyclopentane, cyclopentene, cyclohexane, cyclohexadiene, cycloheptane, and cycloheptatriene. A cyclic alkyl group may be substituted or unsubstituted. Suitable substituents include those described above for alkyl groups.

As used herein, an aryl group refers to an all carbon monocyclic or fused-ring polycyclic group having a completely conjugated pi-electron system. Suitable examples of aryl groups include, but are not limited to, phenyl, benzyl, benzoyl, naphthalenyl, and anthracenyl. The aryl group may be substituted or unsubstituted. Suitable substituents include, but are not limited to, alkyl, hydroxy, alkoxy, aryloxy, thiohydroxy, thioalkoxy, thioaryloxy, cyano, nitro, carbonyl, thiocarbonyl, carboxy, sulfinyl, sulfonyl, amino, halogen, and triohalomethyl.

As used herein, a heteroaryl group refers to a monocyclic or fused ring group having in the ring(s) one or more heteroatoms, such as sulfur, nitrogen, and oxygen, and in addition having a completely conjugated pi-electron system. Suitable heteroaryl groups include, but are not limited to, pyrrole, furan, thiophene, imidazole, oxazole, thiazole, pyrazole, pyridine, pyrimidine, quinoline, isoquinoline, purine, and carbazole. The heteroaryl group may be substituted or unsubstituted. Suitable substituents include, but are not limited to, alkyl, cycloalkyl, hydroxy, alkoxy, aryloxy, thiohydroxy, thioalkoxy, thioaryloxy, cyano, nitro, carbonyl, thiocarbonyl, carboxy, sulfinyl, sulfonyl, amino, halogen, and triohalomethyl.

As used herein, a "combinatorial library" is an intentionally created collection of differing molecules which can be created by the techniques set forth below or otherwise and screened for activity in a variety of formats (e.g., libraries of soluble molecules or libraries of compounds attached to a solid support). A "combinatorial library" involves successive and/or parallel rounds of chemical synthesis based on a common starting structure. The combinatorial libraries can be screened in a variety of assays useful for assessing biological or chemical activities. Compounds disclosed in the prior art that are not in an intentionally created collection are not part of a "combinatorial library" of the present invention. In addition, compounds that are part of an unintentional or undesired mixture are not part of a "combinatorial library" of the present invention.

In accordance with the present invention, the combinatorial library synthesis can be carried out either manually or through the use of an automated process. For manual synthesis, the chemical manipulations would be performed by a scientist or technician. For automated synthesis, the chemical manipulations would typically be performed robotically. The choice and implementation of such techniques is within the skill of one of ordinary skill in the art of combinatorial chemistry and will not be discussed in detail herein.

In one embodiment of the present invention, the combinatorial library includes compounds having the following formula:

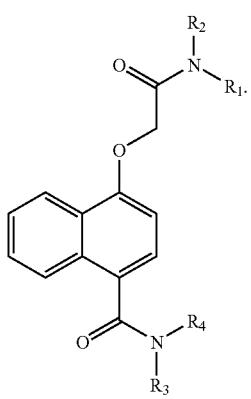

Formula I

In another embodiment of the present invention, the combinatorial library includes compounds having the following formula:

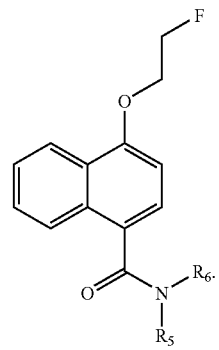

Formula II

In another embodiment of the present invention, the combinatorial library includes compounds having the following formula:

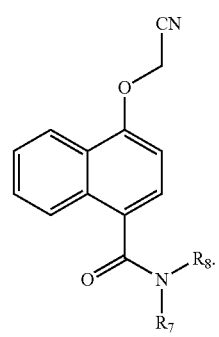

Formula III

In another embodiment of the present invention, the combinatorial library includes compounds having the following formula:

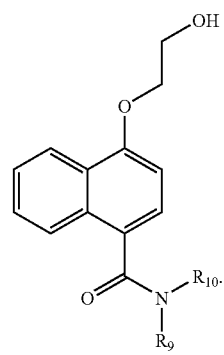

Formula IV

In another embodiment of the present invention, the combinatorial library includes compounds having the following formula:

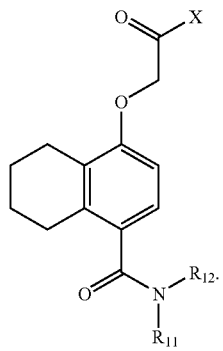

Formula V

In another embodiment of the present invention, the combinatorial library includes compounds having the following formula:

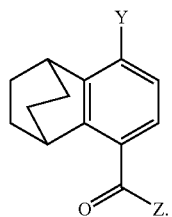

Formula VI

In another embodiment of the present invention, the combinatorial library includes compounds having the following formula:

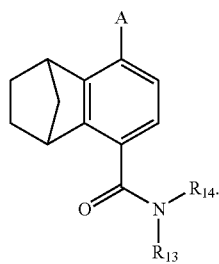

Formula VII

In another embodiment of the present invention, at least one member of the combinatorial library is a protein-protein interaction antagonist. A protein-protein interaction is an interaction between two or more proteins that are contact with each other so as to form a complex comprising of two or more proteins bound to each other. The protein-protein interaction antagonists can be antagonists of transcription factor complexes, such as HOX-PBX, BRN, and Trp repressor, or antagonists of other protein-protein interaction drug targets, such as the ones listed in Berg, *Angew. Chem. Int. Ed.* 42:2462 (2003), which is hereby incorporated by reference in its entirety.

The present invention also relates to a compound having the following formula:

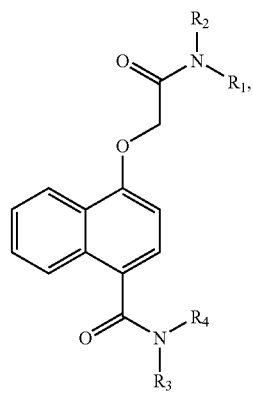

Formula I

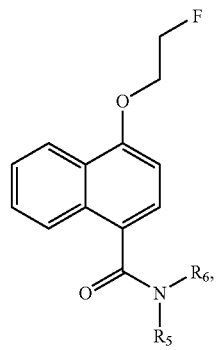

Formula II

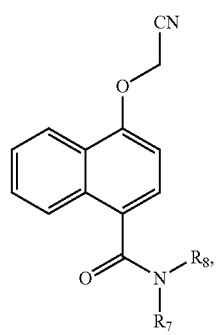

Formula III

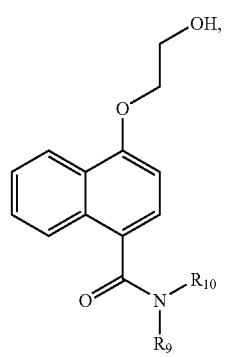

Formula IV

-continued

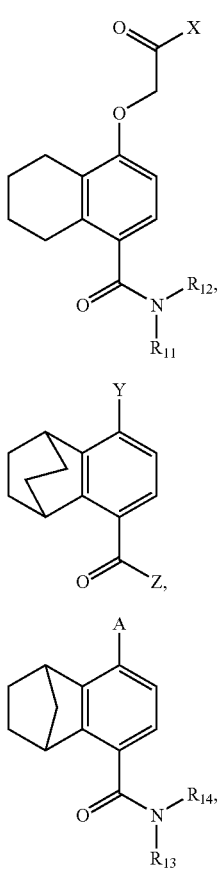

Formula V

Formula VI

Formula VII where:

$R_1$-$R_{14}$ are individually selected from the group consisting of: H, $C_1$-$C_{12}$ alkyl, heteroatom and multiple heteroatom substituted $C_1$-$C_{12}$ alkyl, $C_1$-$C_{12}$ branched or cyclic alkyl, heteroatom and multiple heteroatom substituted $C_1$-$C_{12}$ branched or cyclic alkyl, aryl and substituted aryl, heteroaryl and substituted heteroaryl, alkylaryl and substituted alkylaryl, wherein the substitution includes a heteroatom substitution in the alkyl and/or aryl group, alkylheteroaryl and substituted alkylheteroaryl, amines, $CH_2COOCH_2CH_3$, $CH_2COOH$, and $(CH_2CH_2)_2O$;

$R_1$-$R_{14}$ can optionally be side chains with one or more halogen atoms and functional groups selected from the group consisting of amides, ureas, ketones, sulfonamides, phosphoramides, alcohols, thiols, esters, amines, amidines, guanidines, carboxylic acids, sulfonic acids, phosphonic acids, boronic acids, hydrophilic substituents, and hydrophobic substituents, wherein the functional group can be further substituted with one or more ring heteroatoms or one or more halogens;

X, Y, Z, and A are individually selected from the group consisting of: H, $C_1$-$C_{12}$ alkyl, heteroatom and multiple heteroatom substituted $C_1$-$C_{12}$ alkyl, $C_1$-$C_{12}$ branched or cyclic alkyl, heteroatom and multiple heteroatom substituted $C_1$-$C_{12}$ branched or cyclic alkyl, aryl and substituted aryl, heteroaryl and substituted heteroaryl, alkylaryl and substituted alkylaryl, wherein the substitution includes a heteroatom substitution in the alkyl and/or aryl group, alkylheteroaryl and substituted alkylheteroaryl, amines, $CH_2COOCH_2CH_3$, $CH_2COOH$, and $(CH_2CH_2)_2O$;

X, Y, Z, and A can optionally be side chains with N, S, O, P, or B substituted with any combination of H, $C_1$-$C_{12}$ alkyl, heteroatom and multiple heteroatom substituted $C_1$-$C_{12}$ alkyl, $C_1$-$C_{12}$ branched or cyclic alkyl, heteroatom and multiple heteroatom substituted $C_1$-$C_{12}$ branched or cyclic alkyl, aryl and substituted aryl, heteroaryl and substituted heteroaryl, alkylaryl and substituted alkylaryl, and alkylheteroaryl and substituted alkylheteroaryl, wherein the N, S, or O can also be further attached to a carbonyl, sulfonyl, sulfinyl, or phosphoryl group to form a functional group selected from the group consisting of urea, amide, urethane, sulfonamides sulfinamide, sulfonylurea, sulfinylurea, and phosphoramides ketone, alcohol, thiol, ester, amine, amidine, guanidine, carboxylic acid, sulfonic acid, phosphonic acid, and boronic acid, wherein the functional group can be further substituted with H, $C_1$-$C_{12}$ alkyl, heteroatom and multiple heteroatom substituted $C_1$-$C_{12}$ alkyl, $C_1$-$C_{12}$ branched or cyclic alkyl, heteroatom and multiple heteroatom substituted $C_1$-$C_{12}$ branched or cyclic alkyl, aryl and substituted aryl, heteroaryl and substituted heteroaryl, alkylaryl and substituted alkylaryl, or alkylheteroaryl and substituted alkylheteroaryl, wherein all of the side chains with N, S, O, P, or B can optionally contain one or more halogen atoms and a functional group selected from the group consisting of amide, urea, ketone, sulfonamide, phosphoramide, alcohol, thiol, ester, amine, amidine, guanidine, carboxylic acid, sulfonic acid, phosphonic acid, and boronic acid, or a pharmaceutically acceptable salt thereof.

Specific compounds of the present invention having the structure of above Formula I include, but are not limited to, compounds of the following formulae:

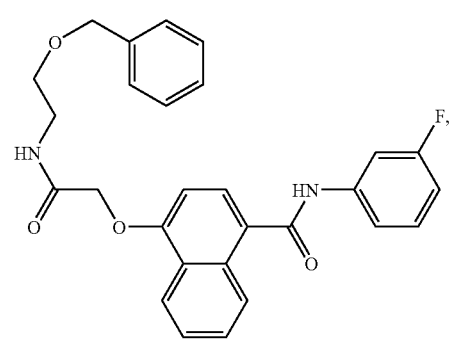

19

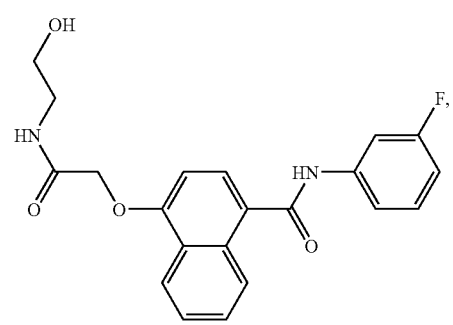

18

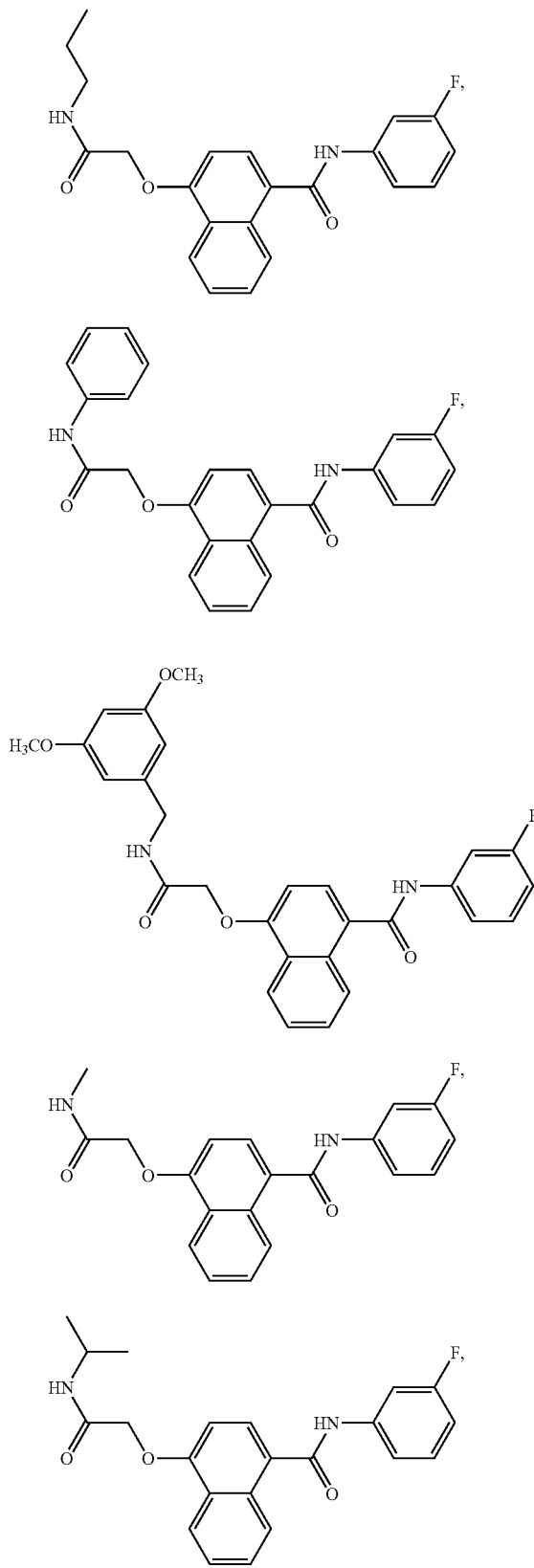
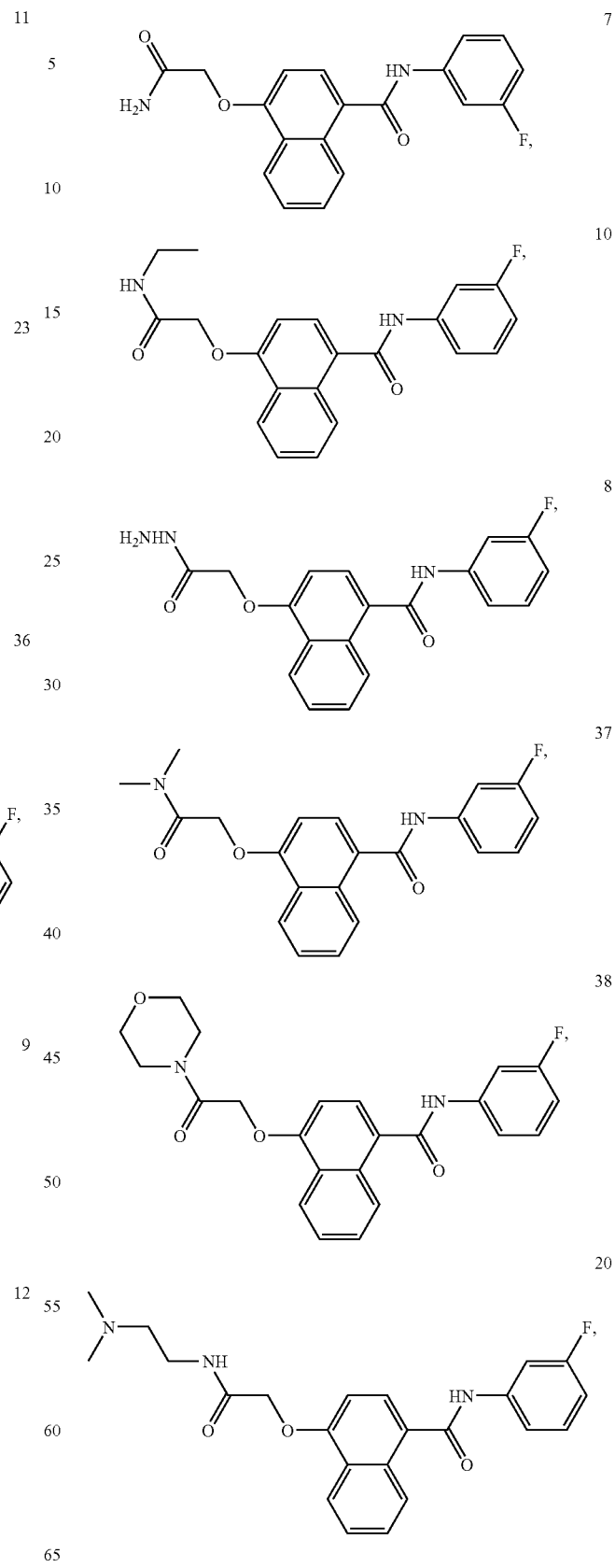

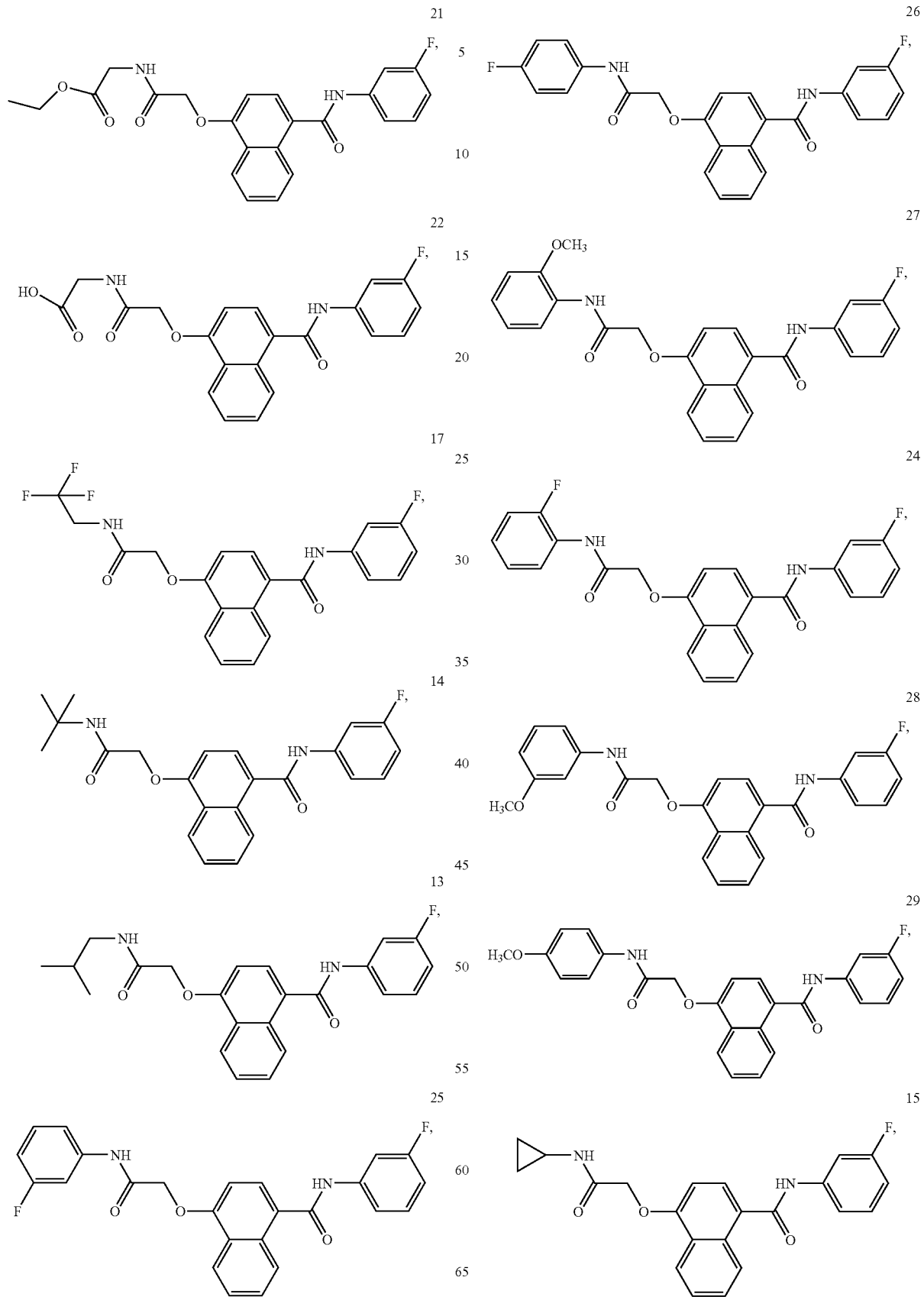

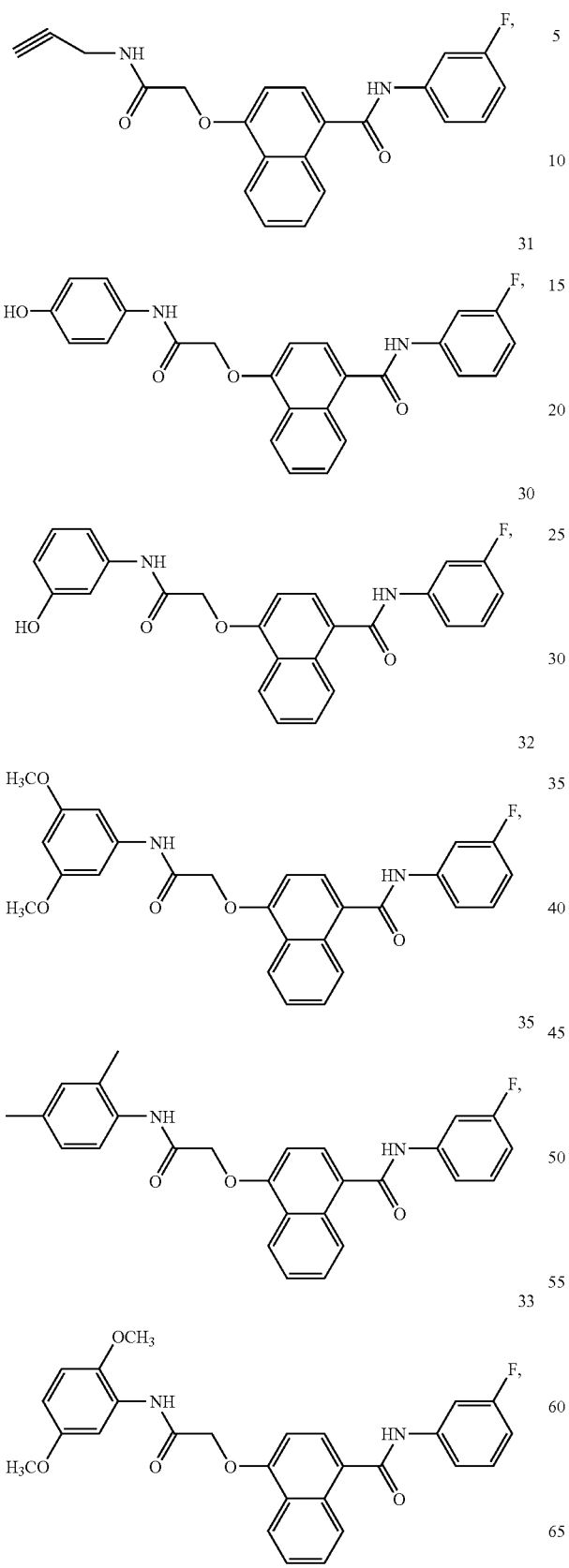
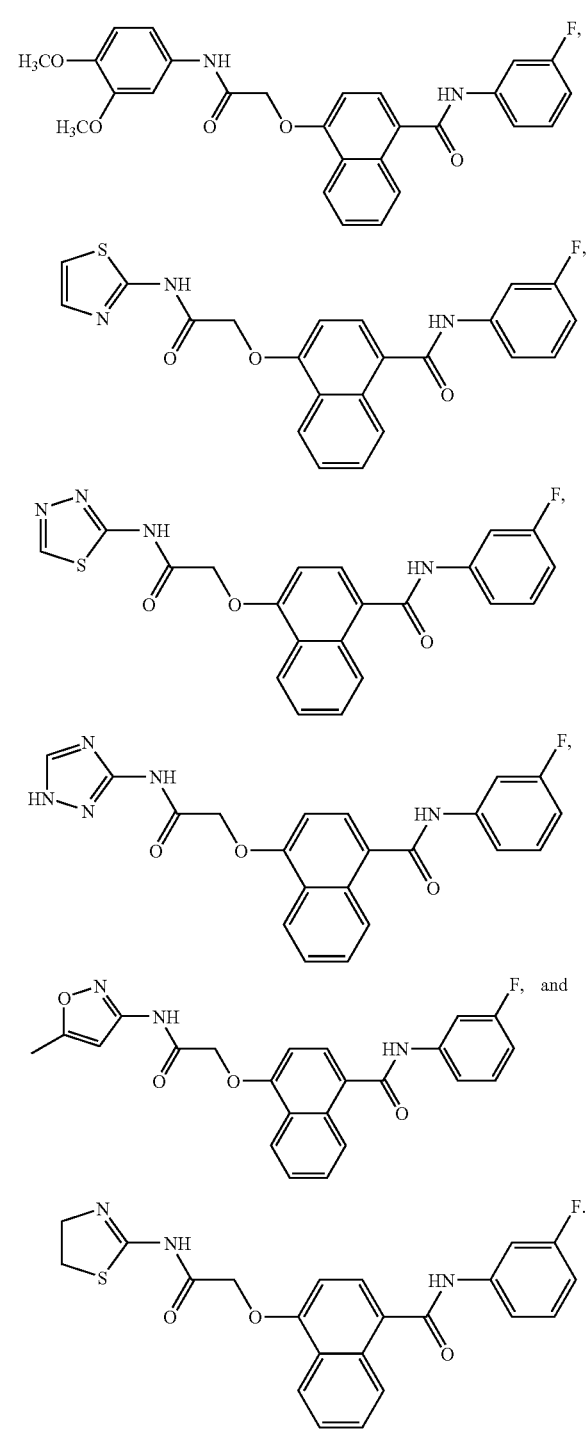
The bold numbers below some of the above compounds correspond to the compound numbers described in Example 1 below.
Specific compounds of the present invention having the structure of above Formula II include, but are not limited to, compounds of the following formulae:

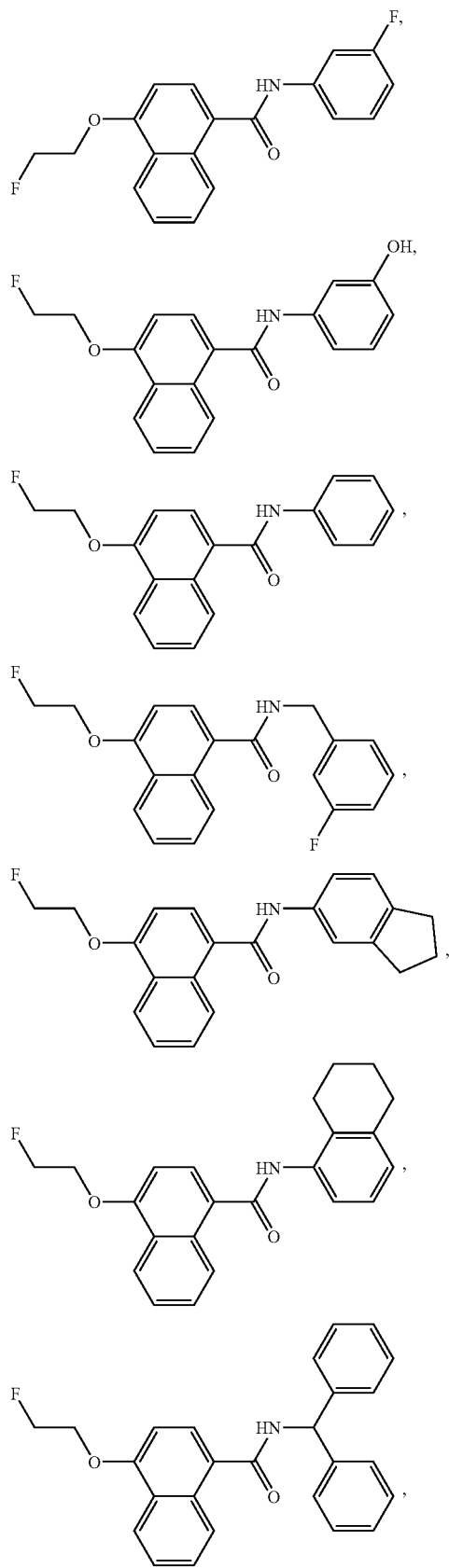
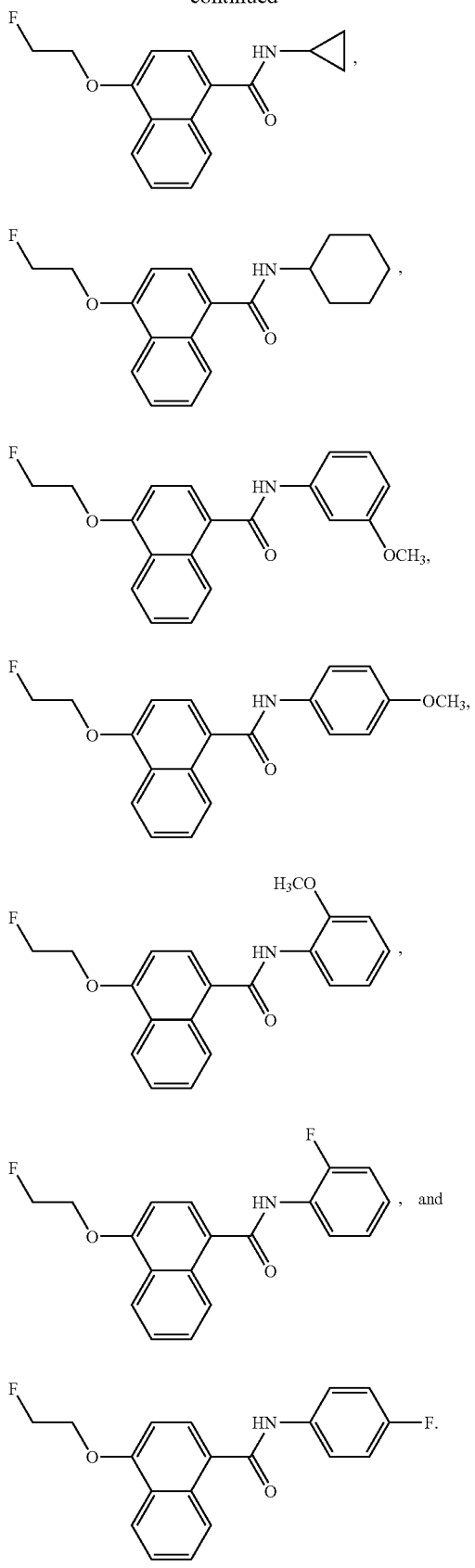

A specific compound of the present invention having the structure of above Formula III include, but are not limited to, a compound of the following formula:

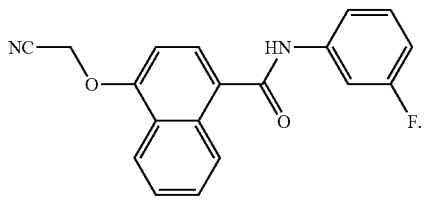

Specific compounds of the present invention having the structure of above Formula IV include, but are not limited to, compounds of the following formulae:

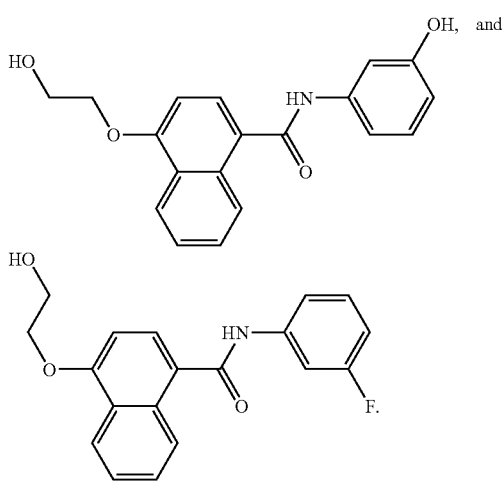

Specific compounds of the present invention having the structure of above Formula V include, but are not limited to, compounds of the following formulae:

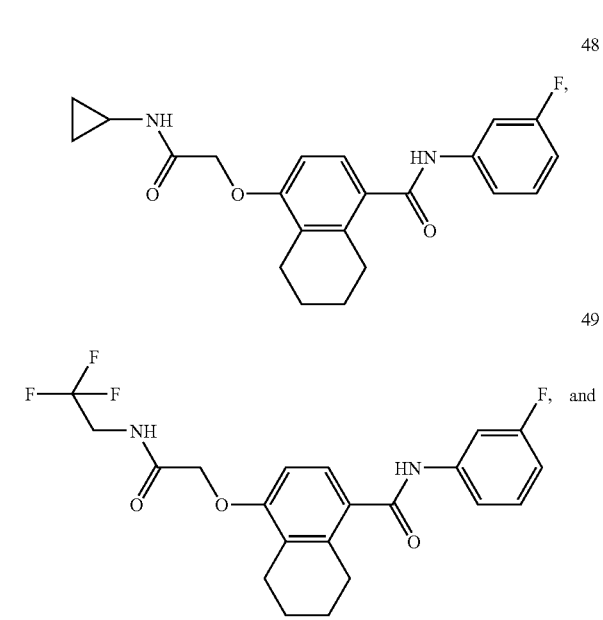

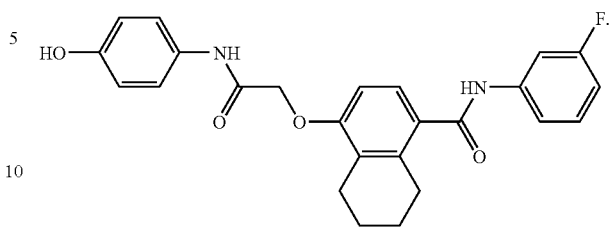

The bold numbers below some of the above compounds correspond to the compound numbers described in Example 2 below.

Specific compounds of the present invention having the structure of above Formula VI include, but are not limited to, compounds of the following formulae:

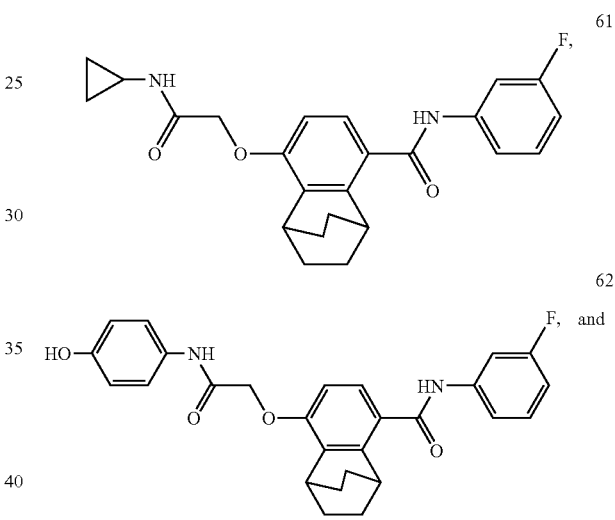

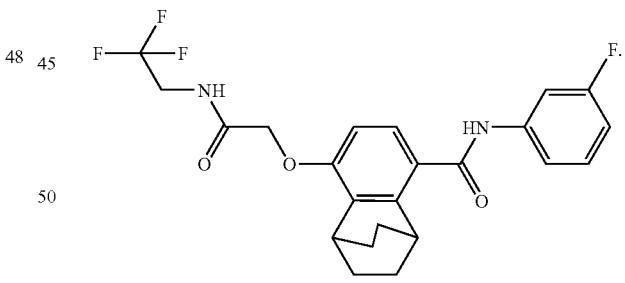

The bold numbers below some of the above compounds correspond to the compound numbers described in Example 3 below.

In another embodiment of the present invention, the compound has a molecular weight of from about 200 Da to about 500 Da.

The compounds in accordance with the present invention, protein-protein interaction antagonists in particular, can be used in compositions which include one or more compounds and a pharmaceutically acceptable carrier.

The compounds and compositions herein can be made up in any suitable form appropriate for the desired use; e.g., oral, parenteral, or topical administration. Examples of parenteral administration are intraventricular, intracerebral, intramuscular, intravenous, intraperitoneal, rectal, and subcutaneous administration. The preferred route for administration is intravenous. In cases where the compounds or compositions are administered topically or parenterally, it is preferred that they be pre-hydrolyzed.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, such as methyl cellulose, tragacanth, sodium alginate; wetting agents, such as lecithin and polyoxyethylene stearate; and preservatives, such as ethyl-p-hydroxybenzoate. Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art.

For oral administration either solid or fluid unit dosage forms can be prepared. For preparing solid compositions, such as tablets, a suitable compound or composition, as disclosed above, is mixed with conventional ingredients, such as talc, magnesium stearate, dicalcium phosphate, magnesium aluminum silicate, calcium sulfate, starch, lactose, acacia methylcellulose, and functionally similar materials as pharmaceutical diluents or carriers. Capsules are prepared by mixing the disclosed compound or compositions with an inert pharmaceutical diluent and filling the mixture into a hard gelatin capsule of appropriate size. Soft gelatin capsules are prepared by machine encapsulation of a slurry of the compound or composition with an acceptable vegetable oil, light liquid petrolatum, or other inert oil.

Fluid unit dosage forms for oral administration such as syrups, elixirs, and suspensions can be prepared. The water-soluble forms can be dissolved in an aqueous vehicle together with sugar, aromatic flavoring agents, and preservatives to form a syrup. An elixir is prepared by using a hydro-alcoholic (ethanol) vehicle with suitable sweeteners, such as sugar and saccharin, together with an aromatic flavoring agent. Suspensions can be prepared with a syrup vehicle with the aid of a suspending agent, such as acacia, tragacanth, methylcellulose, and the like.

For parenteral administration, fluid unit dosage forms are prepared utilizing the aforementioned compound or compositions and a sterile vehicle, water being preferred. The compound or composition, depending on the vehicle and concentration used, can be either suspended or dissolved in the vehicle. In preparing solutions, the compound or composition can be dissolved in water for injection and filter sterilized before filling into a suitable vial or ampule and sealing. Advantageously, adjuvants, such as a local anesthetic, preservative, and buffering agents, can be dissolved in the vehicle. To enhance the stability, the fluid unit dosage form can be frozen after filling into the vial, and the water removed under vacuum. The dry lyophilized powder is then sealed in the vial, and an accompanying vial of water for injection is supplied to reconstitute the liquid prior to use. Parenteral suspensions are prepared in substantially the same manner except that the compound or composition is suspended in the vehicle instead of being dissolved, and sterilization cannot be accomplished by filtration. The compound or composition can be sterilized by exposure to ethylene oxide before suspending in the sterile vehicle. Advantageously, a surfactant or wetting agent is included in the parenteral suspension to facilitate uniform distribution of the compound or composition.

Suitable daily dosages can be based on suitable doses of antibiotics (e.g., carbapenems). Typically, suitable daily doses are from about 10 ng/mL to about 10 mg/mL of the compound or composition (e.g., about 300 mg total for a human). Alternatively, the compound or compositions can be administered orally in foodstuffs.

Alternatively, the compound or composition can be incorporated into a sustained release formulation and surgically implanted using conventional methods. Suitable sustained release matrices include those made of ethylene vinyl acetate and other biocompatible polymers.

For topical administration, carriers, such as phospholipid vesicles, which contain the aforementioned compound or composition may facilitate uptake through the skin.

Another aspect of the present invention relates to a method of identifying a protein-protein interaction antagonist. The method first involves providing a compound as described herein. Next, the compound is contacted with interacting proteins of a protein-protein interaction target complex, whereby the compound is allowed to compete with the interacting proteins. Then, the activity of the compound for inhibiting formation of the protein-protein interaction target complex is measured. Finally, the compound that inhibits formation of the protein-protein interaction target complex is identified as a protein-protein interaction antagonist.

In another embodiment of the present invention, the identified protein-protein interaction antagonist compound is capable of antagonizing additional protein-protein interaction target complexes.

Another aspect of the present invention relates to a method for modulating a protein-protein interaction. The method involves contacting interacting proteins of a protein-protein interaction target with a compound as described herein, whereby the protein-protein interaction between the interacting proteins is modulated. As used herein, modulating a protein-protein interaction means affecting the interaction between two or more proteins in a protein-protein interaction target complex such that the formation of the protein-protein interaction target complex is enhanced or inhibited.

The compounds in accordance with the present invention, protein-protein interaction antagonists in particular, can be used to treat various diseases, such as cancers (e.g., melanoma, lung cancer, and leukemia). (See also Berg, *Angew. Chem. Int. Ed.* 42:2462 (2003), which is hereby incorporated by reference in its entirety.)

EXAMPLES

The following examples are provided to illustrate embodiments of the present invention but are by no means intended to limit its scope.

Example 1

Privileged Scaffolds for Blocking Protein-Protein Interactions: 1,4-Disubstituted Naphthalene Antagonists of Transcription Factor Complex HOX-PBX/DNA A crystal structure of the minimal HOXB1 and PBX1 fragments necessary for cooperative DNA binding has been reported (Piper et al., *Cell* 96:587 (1999), which is hereby incorporated by reference in its entirety). This structure showed that HOXB1 and PBX1 bind to overlapping sites on opposite faces of the DNA double helix. However, the two proteins also bind to each other, and thereby stabilize the ternary complex, where HOXB1 places a short peptide arm (FDWMK; SEQ ID NO: 1) into a hydrophobic binding pocket (a "hot spot") on the surface of PBX1. Previous in vitro studies have shown that disruption of the cooperative DNA binding by HOX to PBX1 proteins can be accomplished by point mutations in this HOX peptide domain (Knoepfler et al., *Mol. Cell. Biol.* 15:5811 (1995), which is hereby incorporated by reference in its entirety). These studies also showed that the Trp 182 (W) and Met 183 (M) residues within the highly conserved pentapeptide region of the HOX family of peptide domains, i.e. F/Y-P/D-W-M-K/R (SEQ ID NO: 2), were critical for cooperative DNA binding with PBX. The crystal structure shows HOXB1 Trp 182 and Met 183 packing against each other and binding in the hydrophobic pocket on the surface of PBX1 (Piper et al., *Cell* 96:587 (1999), which is hereby incorporated by reference in its entirety). This cooperative binding can be competitively blocked by the 12-residue peptide, QPQIYPWMRKLH (SEQ ID NO: 3; $IC_{50}$=100 μM), containing the conserved pentapeptide sequence (Knoepfler et al., *Mol. Cell. Biol.* 15:5811 (1995), which is hereby incorporated by reference in its entirety).

The human HOXB1-PBX1/DNA (code 1B72) complex described above was downloaded from the Protein Data Bank. All molecular modeling, ligand docking and library design studies were carried out using SYBYL 6.8, and the associated modules FlexX, CScore, LeapFrog all obtained from Tripos, Inc. (St. Louis, Mo.). The pentapeptide region of HOXB1 that binds in the hydrophobic pocket on the surface of PBX1 as described above was deleted to expose the critical peptide-binding region for designing small molecule antagonists, and the resulting complex was minimized. A variety of potential scaffolds, with representative appended side chains, were docked into the now exposed hydrophobic pocket and the surrounding surface of PBX1. These candidate scaffolds were selected by a combination of visual evaluation of the binding surface, hand docking of candidate ligands, automated docking (FlexX), de novo design experiments (LeapFrog), ease of synthesis, and predictions of binding affinity (FlexX & CScore). An important criteria that was also applied to the candidate scaffold selection process was the ability to produce potential antagonists with MW<500 and that have the ability to meet the additional "rule of 5" criteria developed by Lipinski et al. for compounds likely to be successful as oral therapeutics (Lipinksi et al., *Advanced Drug Delivery Reviews* 23:3 (1997), which is hereby incorporated by reference in its entirety). Finally, rigid scaffolds that result in antagonists with a limited number of rotatable bonds were given priority since this rigidity is also predicted to improve the probability of obtaining orally active drugs (Veber et al., *J. Med. Chem.* 45:2615 (2002), which is hereby incorporated by reference in its entirety).

With the above criteria in mind, the first scaffold selected for synthesis and testing was the 1,4-disubstituted naphthalene scaffold (Table 1). This rigid scaffold provides two diversity side chains able to interact with the PBX protein at the mouth of the hydrophobic pocket and a phenyl ring to penetrate into the hydrophobic pocket. The library of potential antagonists prepared from this scaffold all had molecular weights between 340 Da (compound 7) and 489 Da (compound 36) and had a limited number of freely rotating bonds (Table 1).

TABLE 1

HOXA1-PBX1/DNA, BRN1/DNA, and BRN2/DNA Antagonist Activity of 1,4-Disubstituted Naphthalenes[a]

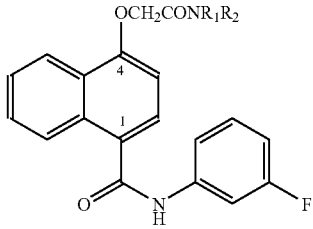

6

| Compound | $R_1$; $R_2$ | HOXA1-PBX1 $IC_{50}$ (μM)[b] | BRN1 $IC_{50}$ (μM)[c] | BRN2 $IC_{50}$ (μM)[c] |
|---|---|---|---|---|
| 7 | H; H | 272 | | |
| 8 | $NH_2$; H | low activity (300 μM) | | |
| 9 | Methyl; H | low activity (300 μM) | | |
| 10 | Ethyl; H | 200 | | |
| 11 | n-Propyl; H | 278 | | |
| 12 | Isopropyl; H | 272 | | |
| 13 | Isobutyl; H | 298 | | |
| 14 | tert-Butyl; H | no activity (300 μM) | | |
| 15 | Cyclopropyl; H | 173 | 810 | >10,000 |
| 16 | Propargyl; H | 331 | | |
| 17 | 2,2,2-Trifluoroethyl; H | 111 | 162 | 204 |
| 18 | 2-Hydroxyethyl; H | no activity (300 μM) | | |
| 19 | 2-Benzyloxyethyl; H | low activity (300 μM) | | |

TABLE 1-continued

HOXA1-PBX1/DNA, BRN1/DNA, and BRN2/DNA Antagonist Activity of 1,4-Disubstituted Naphthalenes[a]

6

[Structure: 1,4-disubstituted naphthalene with OCH$_2$CONR$_1$R$_2$ at position 4 and C(=O)NH-(3-fluorophenyl) at position 1]

| Compound | R$_1$; R$_2$ | HOXA1-PBX1 IC$_{50}$ (μM)[b] | BRN1 IC$_{50}$ (μM)[c] | BRN2 IC$_{50}$ (μM)[c] |
|---|---|---|---|---|
| 20 | 2-Dimethylaminoethyl | no activity (300 μM) | | |
| 21 | —CH$_2$COOCH$_2$CH$_3$; H | no activity (300 μM) | | |
| 22 | —CH$_2$COOH; H | no activity (300 μM) | | |
| 23 | Phenyl; H | 254 | | |
| 24 | 2-Fluorophenyl; H | 433 | | |
| 25 | 3-Fluorophenyl; H | low activity (300 μM) | | |
| 26 | 4-Fluorophenyl; H | 293 | | |
| 27 | 2-Methoxyphenyl; H | 718 | | |
| 28 | 3-Methoxyphenyl; H | 580 | | |
| 29 | 4-Methoxyphenyl; H | 161 | | |
| 30 | 3-Hydroxyphenyl; H | 86 | 142 | 148 |
| 31 | 4-Hydroxyphenyl; H | 65 | 124 | 138 |
| 32 | 3,5-Dimethoxyphenyl; H | low activity (300 μM) | | |
| 33 | 2,5-Dimethoxyphenyl; H | low activity (300 μM) | | |
| 34 | 3,4-Dimethoxyphenyl; H | 464 | | |
| 35 | 2,4-Dimethylphenyl; H | low activity (300 μM) | | |
| 36 | 3,5-Dimethoxybenzyl; H | no activity (300 μM) | | |
| 37 | Methyl; methyl | no activity (300 μM) | | |
| 38 | R$_1$, R$_2$ = (CH$_2$CH$_2$)$_2$O | no activity (300 μM) | | |

[a]Determined by electrophoretic mobility shift assay (EMSA). IC$_{50}$ data results from an averaged densitometric analysis of multiple EMSA gels.
[b]2.5 ng each of the mouse HOXA1 192-288 protein and the mouse/human 233-319 PBX1 protein in a final volume of 25 μl binding buffer containing 10 mM HEPES, pH 7.9, 1 mM EDTA, 1 mM DTT, 5% Ficoll-400, 0.1 mg/ml BSA, and 135 mM NaCl was pre-incubated for 15 minutes at 4° C. with 0.5 μg poly dIdC (to reduce non-specific DNA binding) and 1 μl of an appropriate dilution of the inhibitory compound in DMSO. Proteins in binding buffer were incubated for 30 minutes at approximately 22° C. with 1 μl of $^{32}$P labeled oligonucleotide probe prepared as described below (1–2 × 10$^4$ CPM) prior to electrophoresis on a 4% polyacrylimide gel in 50 mM TBE buffer at 150 V for 2 hr 15 min. Two oligonucleotides, HOXPBX-CT Top, 5'CTCTC-CTTTTGATTGATTAA-3' (SEQ ID NO: 4) and HOXPBX-CT Bottom 5'-AGAGCTTAATCAATCAAAAGG-3' (SEQ ID NO: 5) were annealed and the ends extended with Klenow in the presence of α32P-dCTP to prepare the oligonucleotide probes. Following electrophoresis, gels were dried and exposed to X-ray autoradiographic film for 18 to 24 h.
[c]EMSAs were performed with BRN1 and BRN2 exactly as was done with HOXA1-PBX1 when using nuclear extracts from RA treated P19 cells (for BRN induced by RA in P19 cells see Bain et al., Bioessays 16:343 (1994), which is hereby incorporated by reference in its entirety) except that a sequence recognition element known to bind BRN1 or BRN2 monomers was used as the probe (Pruitt et al. Gene Expression Patterns 4(6): 671 (2004), which is hereby incorporated by reference in its entirety).

A modeled complex (after minimization) of the parent inhibitor based upon this scaffold, compound 7 showed that the naphthalene ring was positioned within the hydrophobic pocket, the C-1 amide side chain NH was forming a hydrogen bond with Leu-252 and the 3-fluoro atom on the phenyl amide side chain was hydrogen bonding with Tyr-291. The C-4 ether amide side chain was extending across the surface of PBX1 in the direction of the bound DNA. From these modeling studies the C-4 side chain appeared to have multiple potential binding opportunities, so a range of side chains at this position was selected for experimental evaluation (Table 1).

A focused combinatorial library of thirty-two 1,4-disubstituted naphthalene derivatives with the modeled 3-fluorophenyl amide C-1 side chain and various ether amide side chains at C-4 were synthesized (Scheme 1). The synthesis begins from commercially available 4-methoxy-1-naphthaldehyde 1, as outlined in Scheme 1. Oxidation of aldehyde 1 provided acid 2 (Ahmed et al., *Tetrahedron Lett.* 42:3407 (2001), which is hereby incorporated by reference in its entirety). Amide 3 was obtained by coupling the corresponding acid chloride with 3-fluoroaniline. Demethylation of methyl ether 3 using AlCl$_3$/EtSH produced the corresponding phenol (Node et al., *J. Org Chem.* 45:4275 (1980), which is hereby incorporated by reference in its entirety), which was then converted to methyl ester 4. Acid 5 was obtained by refluxing ester 4 with LiOH in methanol. The final target amides 6 were synthesized using 1-benzotriazolyoxytris(pyrrolidino)phosphonium hexafluorophosphate (PyBOP) as the coupling reagent with a broad range of amines. All final products were purified by silica gel chromatography to greater than 95% purity and gave $^1$H NMR and MS spectra that are consistent with the expected product.

Scheme 1

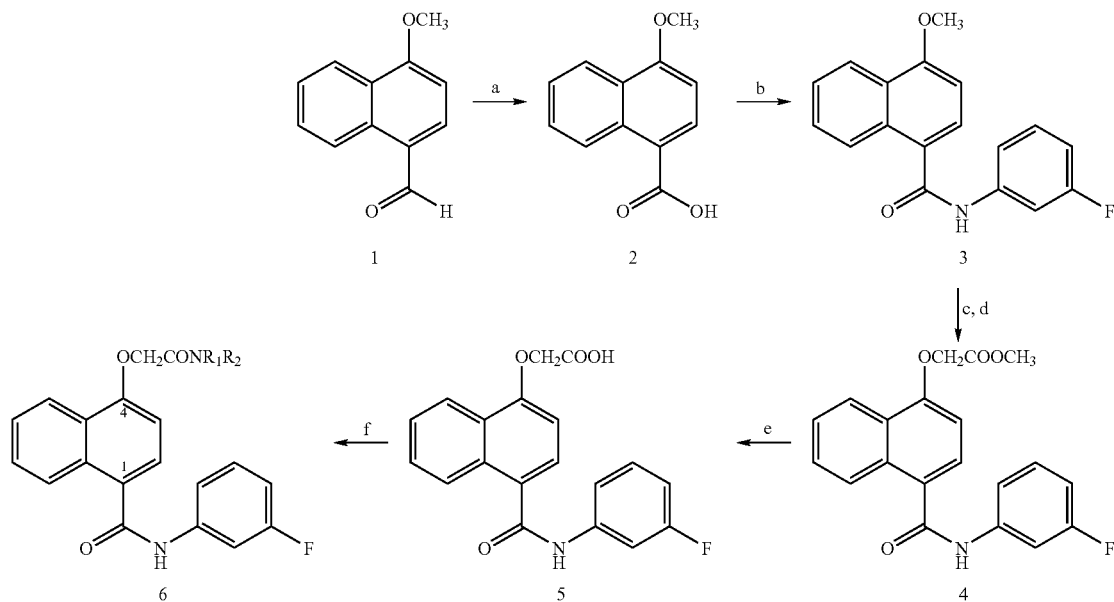

a) NaClO$_2$, NaH$_2$PO$_4$, H$_2$O, t-BuOH, 2-methyl-2-butene, room temperature, 24 h, 95%;
b) (1) SOCl$_2$, CH$_2$Cl$_2$, reflux (50° C.), 6 h; (2) 3-Fluoroaniline, tetrahydrofuran (THF), N,N-diisopropylethylamine (DIEA), reflux, 0.5 h, 90%;
c) AlCl$_3$, CH$_3$CH$_2$SH, CH$_2$Cl$_2$, 0° C. to room temperature, 2 h, 93%;
d) BrCH$_2$COOCH$_3$, K$_2$CO$_3$, THF, reflux, 1 h, 100%;
e) LiOH, MeOH, H$_2$O, reflux, 2 h, 95%;
f) PyBOP, R$_1$R$_2$NH, N,N-dimethylforamide (DMF), 0° C. to room temperature, 2 h, 90~95%.

The selectivity of individual members of the library for the HOXA1-PBX1/DNA target, as well as the ability of some analogs to cross over to other transcription factor targets was evaluated by testing them in parallel against the BRN1 & BRN2 transcription factors. BRN1 and BRN2 are members of mammalian class III POU transcription factor family and are expressed in the developing embryonic brain (McEvilly et al., *Science* 295:1528 (2002), which is hereby incorporated by reference in its entirety). POU domain class transcription factors contain, in addition to the POU domain, a homeodomain helix-turn-helix class DNA binding motif similar to that found in the HOX and PBX class transcription factors (Josephson et al., *Development* 125:3087 (1998); Hara et al., *PNAS* 89(8):3280 (1992), which are hereby incorporated by reference in their entirety). EMSAs were performed with BRN1 & BRN2 exactly as was done with HOXA1-PBX1 except that a sequence recognition element known to bind BRN1/BRN2 was used as the probe (Pruitt et al., *Gene Expression Patterns* 4(6):671 (2004), which is hereby incorporated by reference in its entirety).

Of the 32 analogs listed in Table 1, twenty four analogs showed measurable inhibition of the formation of the HOX1-PBX1/DNA ternary complex when screened at a 300 μM initial concentration. A relatively high initial screening concentration was chosen for two reasons: (1) the known 12-residue peptide antagonist, QPQIYPWMRKLH (SEQ ID NO: 3), containing the conserved pentapeptide sequence (underlined) that binds to the Pbx1 hydrophobic pocket, has an IC$_{50}$ of only 100 μM; (2) protein-protein interaction targets are significantly more challenging to block with small molecules than the classical drug targets for which lower screening concentrations can be used.

Of these twenty four active compounds against the HOXA1-PBX1/DNA target, the most potent were compounds 30 and 31 with IC$_{50}$s=86 and 65 μM, respectively. These compounds were more potent than the much larger 12-residue peptide antagonist QPQIYPWMRKLH (SEQ ID NO: 3) containing the conserved pentapeptide sequence (Knoepfler et al., *Mol. Cell. Biol.* 15:5811 (1995), which is hereby incorporated by reference in its entirety) and differ from each other only by the position of the hydroxyl group in the C-4 aryl amide moiety.

FIG. 1 illustrates that compound 31 inhibited the formation of the PBX1/DNA binary complex as well the ternary HOX1-PBX1/DNA complex, whereas compound 15 inhibited formation of ternary complex only. Antagonist 31 differs from compound 15 by replacing the small cyclopropyl R$_1$ with the larger 4-hydroxyphenyl group. The modeled complex indicated that these substituents are directed towards the bound DNA. Consequently, the larger 4-hydroxyphenyl group may be altering the conformation of the PBX1/DNA binary complex so as to destabilize it, whereas the smaller cyclopropyl group does not extend far enough into the DNA binding region to do this. On the other hand, both antagonists can bind in the hydrophobic pocket thereby preventing HOXA1 from binding to the binary complex. Upon closer evaluation of the compound 31 dose-response of the binary PBX/DNA band intensity relative to the ternary HOXA1-PBX/DNA band intensity, it was noted that the binary PBX/DNA band initially "increased" in intensity at low compound 31 concentrations. One potential explanation for this result is that HOXA1 is released from the ternary complex generating a higher initial concentration of the binary complex. As the concentration of compound 31 is further increased, the binary PBX/DNA complex formation is inhibited enough to overcome the release of this binary complex from the ternary complex and, therefore, the binary band intensity begins to decrease.

Collectively, the above results suggest that compounds based on the 1,4-disubstitued naphthalene scaffold are binding to PBX1 rather than directly binding to DNA. If compound 15 were directly binding to DNA, then it would need to be binding to a region of the DNA not contacted by PBX1 in order to explain the selective inhibition of the formation of the HOXA1-PBX1/DNA ternary complex versus the PBX1/DNA binary complex. Likewise, if compound 31 were directly binding to DNA, then it would need to be binding to a region of DNA not contacted by PBX1 since low concentrations of compound 31 "increase" the concentration of the PBX1/DNA binary complex. Since both results are more readily explained by binding of the compounds in the pentapeptide binding pocket for which they have complementary topological features by design, it is likely that the mechanism of inhibition is direct binding to PBX1.

FIG. 1 illustrates that compound 15 was also selective towards the HOXA1-PBX1/DNA target ($IC_{50}$=173 μM) versus BRN1/DNA ($IC_{50}$=810 μM) or BRN2/DNA ($IC_{50}$=>10,000 μM). This result again suggests direct binding to PBX1 rather than to DNA. Extension 15 from the pentapeptide pocket into the DNA binding region provided compound 31 which now inhibits BRN1 and BRN2 from binding to their recognition sequences with $IC_{50}$s of 124 μM and 138 μM, respectively, versus 65 μM against HOXA1-PBX1/DNA. Overall, compound 15 is selective for blocking the HOXA1-PBX1/DNA ternary complex relative to all of the other complexes tested, whereas compound 31 is an active antagonist of all of the complexes with some selectivity for the HOXA1-PBX1/DNA complex. Since compound 31 can extend into the DNA binding region of the PBX1/DNA complex and thereby block DNA from binding, BRN1 and BRN2 may have similar hydrophobic pockets resulting in the ability of compound 31 to block DNA from binding to them as well.

The ability of the 1,4-disubstituted naphthalenes to cross over from PBX to the BRN transcription factors and antagonize their DNA complex, when suitable side chains are present, suggests that this may be a privileged scaffold for related transcription factors. The known tendency (Breinbauer et al., *Angew. Chem. Int. Ed.* 41:2878 (2002), which is hereby incorporated by reference in its entirety) of proteins to reuse general binding motifs for a new purpose, after evolving the necessary modifications to attain a new function, suggests that the PBX hydrophobic pocket targeted by these antagonists may be reused in BRN and other transcription factor complexes. Consequently, larger screening libraries based upon this scaffold may produce antagonists, including more potent ones, of various members of this class of transcription factors. A library of such antagonists, including those selective for ternary versus binary complexes, as discovered herein, would serve as valuable bio-probes (or drug leads) for investigating the role of these transcription factors in various biological processes and diseases.

Example 2

Synthesis of 1,4-Disubstituted 5,6,7,8-Tetrahydro-naphthalene Derivatives

The synthesis of 1,4-disubstituted 5,6,7,8-tetrahydro-naphthalene derivatives 47 began from methylation of 5,6,7,8-tetrahydro-1-naphthol (Scheme 2). 4-acyl tetralin 41 was exclusively obtained by Friedel-Crafts acylation of 40, using acetyl chloride (Parlow, *Tetrahedron* 50:3297 (1994), which is hereby incorporated by reference in its entirety). The structure assignment of 4-acyl tetralin was determined by 1D nuclear Overhauser effect (NOE). A haloform reaction was used to convert methyl ketone 41 to free acid 42 (Arnold et al., *J. Am. Chem. Soc.* 66:20 (1944), which is hereby incorporated by reference in its entirety). The following steps of preparation of compound 47 in Scheme 2 are based on the same reaction scheme as Scheme 1 described above that converted 2 to 7.

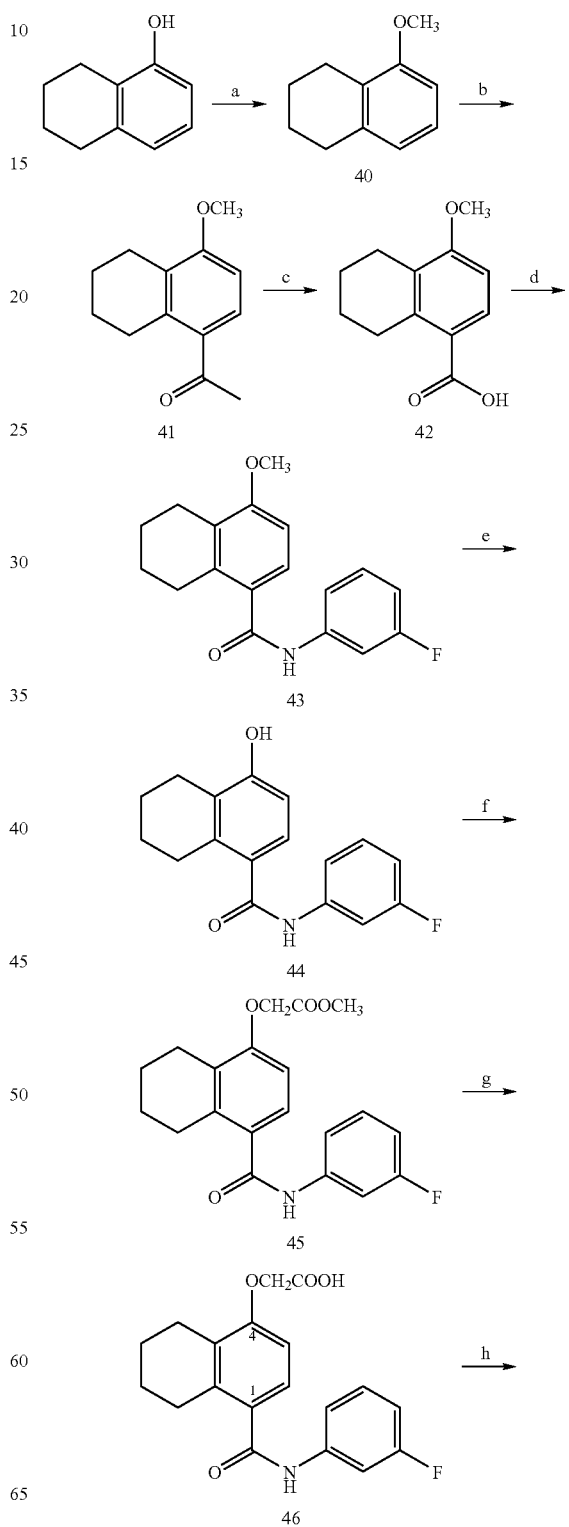

-continued

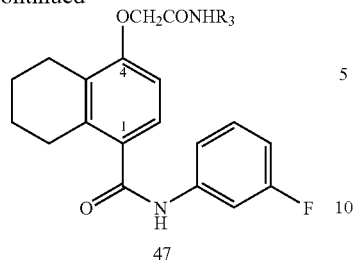

a) CH₃I, K₂CO₃, CH₃COCH₃, reflux, overnight, 100%;
b) CH3COCl, AlCl₃, ClCH₂CH₂Cl, 0° C., 80%;
c) KClO, KOH, K₂CO₃, MeOH, H₂O, 0° C. to room temperature 1 h then reflux 1 h 100%;
d) (1) SOCl₂, CH₂Cl₂, reflux (50° C.), 6h; (2) 3-Flouroaniline, THF, DIEA, reflux, 0.5 h, 100%;
e) AlCl₃, CH₃CH₂SH, CH₂Cl₂, 0° C. to room temperature, 2 h, 95%;
f) BrCH₂COOCH₃, K₂CO₃, acetone, reflux, 1 h, 98%;
g) LiOH, MeOH, H₂O, reflux, 2 h, 95%;
h) PyBOP, R₃NH₂, DIEA, DMF, 0° C. to room temperature, 2 h, 90~95%.

Preparation of
5-Methoxy-1,2,3,4-tetrahydro-naphthalene
(Compound 40)

The mixture of 5,6,7,8-tetrahydro-1-naphthol (5 g, 33.74 mmol), iodomethane (4.8 g, 33.74 mmol), anhydrous $K_2CO_3$ in 20 ml dry acetone was heated to reflux (45° C.) overnight. The solvent was removed and the residue was added to 50 ml water and extracted with 3×20 ml ethyl acetate. The organic layer was combined and washed with 30 ml brine, dried over anhydrous $Na_2SO_4$, filtered, and the solvent was removed to give the crude product. The crude product was purified by column chromatography to afford 5.47 g (100%) of 40. ¹HNMR (400 M, $CD_3COCD_3$) δ 1.73 (m, 4H), 2.59 (t, 2H), 2.70 (t, 2H), 3.78 (s, 3H), 6.64 (d, 1H), 6.77 (d, 1H), 7.02 (s, 1H). MS (EI) m/z: 162($M^+$).

Preparation of 1-(4-Methoxy-5,6,7,8-tetrahydro-naphthalen-1-yl)-ethanone (Compound 41)

A solution of 4.8 g (29.6 mmol) of 40 in 1,2-dichloroethane (30 ml) was added dropwise to a cold (0° C.) solution of acetyl chloride and anhydrous $AlCl_3$ in 100 ml $ClCH_2CH_2Cl$. The mixture was stirred for an additional 30 min at 0° C. after complete addition. The solution was poured to 200 ml ice/water. The organic layer was washed with water and brine. The solution was dried over sodium sulfate, filtered, and the solvent was removed to give the crude product. The crude product was purified by column chromatography to afford 4.08 g (80%) of 41. ¹HNMR (500 M, $CD_3COCD_3$) δ 1.69 (m, 4H), 2.48 (s, 3H), 2.62 (t, 2H), 2.96 (t, 2H), 3.88 (s, 3H), 6.83 (d, 1H), 7.20 (d, 1H). MS (EI) m/z: 204($M^+$).

Preparation of 4-Methoxy-5,6,7,8-tetrahydro-naphthalen-1-carboxylic Acid (Compound 42)

A warm solution of 52.5 g (0.378 mol) $K_2CO_3$ and 6 g (0.107 mmol) KOH in 150 ml $H_2O$ was added to a solution of 75 g (0.524 mol) calcium hypochlorite in 300 ml hot water. The mixture was filtered and the precipitate was washed with 60 ml water. The hypochlorite solution was slowly added to 5 g (24.5 mmol) of 41 in 75 ml methanol with ice bath. The mixture was stirred for an additional 0.5 h at room temperature after complete addition. A sodium sulfite solution was added to destroy excess hypochlorite; then, the mixture was heated to reflux for 1 h. The solution was poured to ice/hydrochloric acid (200 g), filtered, and 5.0 g (100%) of white solid was obtained. ¹HNMR (300 M, DMSO-$D_6$) δ 1.65 (m, 4H), 2.55 (t, 2H), 2.97 (t, 2H) 3.80 (s, 3H), 6.83 (d, 1H), 7.69 (d, 1H), 12.30 (s, 1H); MS (EI) m/z: 206($M^+$); mp 214-215° C.

Preparation of 4-Methoxy-5,6,7,8-tetrahydro-naphthalene-1-carboxylic Acid (3-fluoro-phenyl)-amide (Compound 43)

A mixture of thionyl chloride (1.74 g, 14.6 mmol) and acid 42 (2.0 g, 9.7 mmol) in 20 ml dichloromethane was heated to reflux for 6 h. The solvent was removed in vacuo and pale crude acid chloride was dissolved in 20 ml of dry THF and treated with 1.88 g (14.6 mmol) DIEA and 3-flouroaniline (1.29 g, 11.6 mmol). The mixture was warmed to reflux for 0.5 h and poured into cold 1 M HCl solution, filtered, and a white crude product was obtained. The crude product was purified by column chromatography to afford 2.9 g (100%) of 43. ¹HNMR (300 M, $CD_3COCD_3$) δ 1.68 (m, 4H), 2.59 (t, 2H), 2.77 (t, 2H), 3.80 (s, 3H), 6.83~6.91 (m, 2H), 7.26~7.44 (m, 1H), 7.50 (m, 1H), 7.69 (d, 2H), 10.32 (s, 1H). MS (EI) m/z: 299($M^+$).

Preparation of 4-Hydroxy-5,6,7,8-tetrahydro-naphthalene-1-carboxylic Acid (3-fluoro-phenyl)-amide (Compound 44)

To a mixture of ethylthiol (9 ml) and dry dichloromethane (20 ml) was added $AlCl_3$ (1.76 g, 13.2 mmol) at 0° C. 43 was added slowly to the resulting solution with stirring and then stirred at room temperature for 1.5 h and poured to ice/water, filtered, and a white crude product was obtained. The crude product was purified by column chromatography to afford 2.63 g of 44 (95%). ¹HNMR (300 M, DMSO-$D_6$) δ 1.68 (m, 4H), 2.76 (t, 2H), 2.95 (t, 2H), 6.86 (d, 1H), 7.06 (m, 1H), 7.32 (d, 1H), 7.53 (m, 1H), 7.64 (m, 1H), 7.88 (d, 1H), 9.86 (s, 1H), 10.43 (s, 1H). MS (EI) m/z: 285($M^+$).

Preparation of [4-(3-Fluoro-phenylcarbamoyl)-5,6,7,8-tetrahydro-naphthalen-1-yloxy]-acetic Acid Methyl Ester (Compound 45)

A mixture of 44 (2.3 g, 8 mmol), methyl bromoacetate (1.35 g, 8.8 mmol) and anhydrous $K_2CO_3$ (1.66 g, 12 mmol) was heated to reflux for 1 h. The reaction mixture was dumped into cold 1 M HCl solution, filtered, and a white crude product was obtained. The product was purified by column chromatography to afford 2.86 g of 45 (98%). ¹HNMR (400 M, DMSO-$D_6$) δ 1.66 (m, 4H), 2.66 (t, 2H), 2.76 (t, 2H), 3.69 (s, 3H), 4.87 (s, 2H), 6.75 (d, 1H), 6.88 (m, 1H), 7.22 (d, 1H), 7.32 (m, 1H), 7.44 (m, 1H), 7.68 (d, 1H), 10.36 (s, 1H). MS (EI) m/z: 357($M^+$).

Preparation of [4-(3-Fluoro-phenylcarbamoyl)-5,6,7,8-tetrahydro-naphthalen-1-yloxy]-acetic Acid (Compound 46)

A mixture of 45 (3.46 g, 9.7 mmol), LiOH (0.93 g, 38.8 mmol) in 30 ml MeOH and 15 ml water was heated to reflux for 1 h. The reaction mixture was diluted with 50 ml water and acidified with 2M HCl solution to pH=2~3, filtered, and 3.18 g (95%) of a white solid was obtained. ¹HNMR (400 M, DMSO-$D_6$) δ 1.69 (m, 4H), 2.66 (t, 2H), 2.76 (t, 2H), 4.74 (s, 2H), 6.73 (d, 1H), 6.88 (m, 1H), 7.23 (d, 1H), 7.34 (m, 1H), 7.30 (m, 1H), 7.69 (d, 1H), 10.35 (s, 1H). MS (EI) m/z: 343($M^+$).

General Procedure for Amide Coupling

A mixture of amine (0.3 mmol), acid (0.3 mmol) and DIEA (0.6 ml) in 1 ml anhydrous DMF was cooled to 0° C. PyBOP (0.3 mmol as 0.3 ml of 1 M solution in DMF) was added. The mixture was stirred at 0° C. for 30 minutes and then at room temperature for 2 h. The mixture was poured into 1M HCl solution and a solid was collected with filtration. The crude product was purified by recrystallization or column chromatography.

For [4-cyclopropylcarbamoxy-5,6,7,8-tetrahydro-naphthalen-1-carboxylic acid](3-fluoro-phenyl)-amide (compound 48): $^1$HNMR (300 M, DMSO-$D_6$) δ 0.47 (m, 2H), 0.62 (m, 2H), 1.69 (m, 4H), 2.49~2.68 (m, 3H), 2.78 (t, 2H), 4.48 (s, 2H), 6.78 (d, 1H), 6.88 (m, 1H), 7.29 (d, 1H), 7.35 (m, 1H), 7.40 (m, 1H), 7.69 (d, 1H), 8.03 (d, 1H), 10.34 (s, 1H). HR-MS (ESI) m/z: 383.1750 ($MH^+$, requires 383.1754).

For [4-[(2,2,2-Trifluoro-ethylcarbamoyl)-5,6,7,8-tetrahydro-naphthalen-1-carboxylic acid](3-fluoro-phenyl)-amide (compound 49): $^1$HNMR 400 M, DMSO-$D_6$) δ 1.66~1.73 (m, 4H), 2.71 (t, 2H), 2.78 (t, 2H), 3.96 (m, 2H), 4.65 (s, 2H), 6.71 (d, 1H), 6.88 (m, 1H), 7.24 (d, 1H), 7.33 (m, 1H), 7.45 (m, 1H), 7.68 (d, 1H), 8.64 (d, 1H), 10.36 (s, 1H). HR-MS (ESI) m/z: 425.1473 ($MH^+$, requires 425.1471).

For [4-[(4-hydroxy-phenylcarbamoyl)-5,6,7,8-tetrahydro-naphthalen-1-carboxylic acid](3-fluoro-phenyl)-amide (compound 50): $^1$HNMR (400 M, DMSO-$D_6$) δ 1.69~1.72 (m, 4H), 2.74 (t, 2H), 2.81 (t, 2H), 4.73 (s, 2H), 6.71 (d, 2H), 6.79 (d, 1H), 6.90 (m, 1H), 7.27 (d, 1H), 7.31~7.41 (m, 3H), 7.46 (m, 1H), 7.70 (d, 1H), 9.26 (s, 1H), 9.83 (s, 1H), 10.36 (s, 1H). HR-MS (ESI) m/z: 435.1711 ($MH^+$, requires 435.1715).

Table 2 below shows the HOXA1/PBX1/DNA antagonist activities of several 1,4-disubstituted 5,6,7,8-tetrahydro-naphthalene derivatives, compounds 48, 49, and 50 in particular.

TABLE 2

HOXA1/PBX1/DNA Antagonist Activity of 1,4-Disubstituted 5,6,7,8-Tetrahydro-naphthalenes

47

40

| Compound | $R_3$ | HOXA1/PBX1 $IC_{50}$ (μM)$^a$ |
|---|---|---|
| 48 | cyclopropyl | 66 |
| 49 | 2,2,2-trifluoroethyl | 84 |
| 50 | 4-hydroxyphenyl | 96 |

Example 3

Synthesis of 3,6-Disubstituted Tricyclo[6.2.2.0$^{2,7}$]dodeca-2(7),3,5-triene Derivatives The synthesis of 3,6-disubstituted tricyclo[6.2.2.0$^{2,7}$]dodeca-2(7),3,5-triene derivatives 60 (Scheme 3) began from hydrogenation of p-benzoquinone and cyclohexa-1,3-diene adduct (Fang et al., *Synthetic Communications* 30:2669 (2000), which is hereby incorporated by reference in its entirety) over Pd/C (Birney et al., *J. Am. Chem. Soc.* 124 (2002), which is hereby incorporated by reference in its entirety). Tricyclo[6.2.2.0$^{2,7}$]dodecane-3,6-dione 52 was converted to 3-ethoxy Tricyclo[6.2.2.0$^{2,7}$]dodecane-2,4,6-triene 53 by heating diketone 52, ethanol, p-toluenesulphonic acid, and toluene under a soxhlet extractor filled with anhydrous $Mg_2SO_4$ (Alder et al., *J. Chem. Soc. Abstracts* 4598 (1963), which is hereby incorporated by reference in its entirety). The following steps of preparation of compound 60 in Scheme 3 are based on the same reaction scheme as Scheme 2 described above that converted 40 to 47.

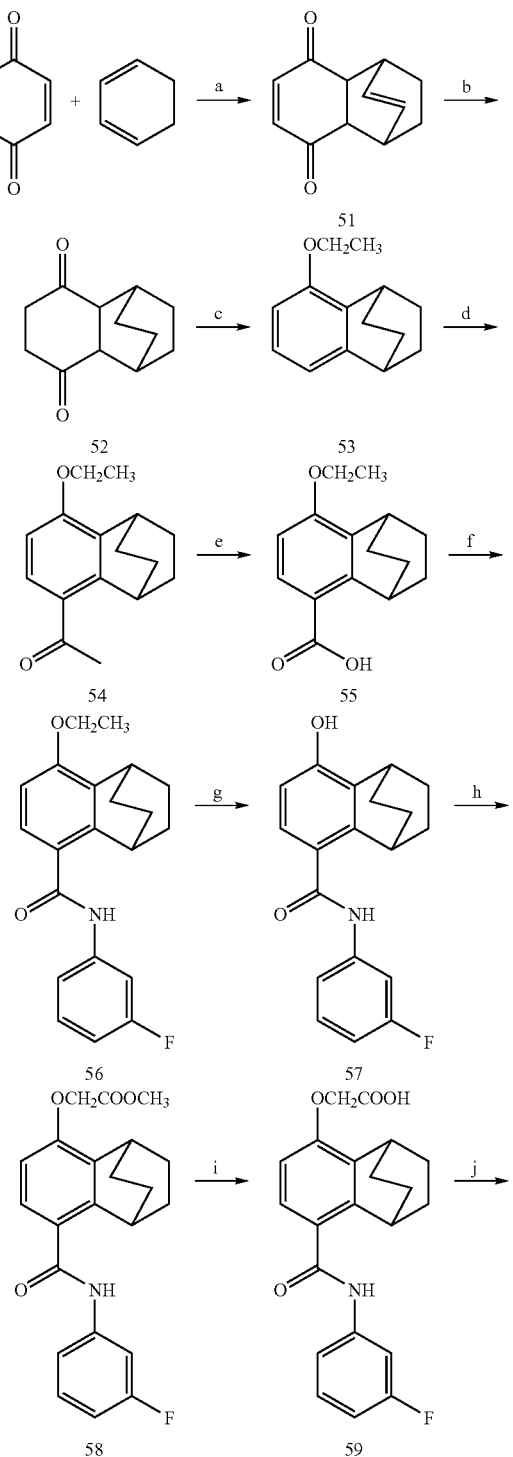

Scheme 3

-continued

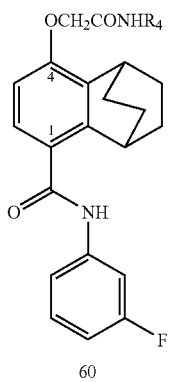

a) YbCl$_3$, CH$_2$Cl$_2$, room temperature, 5 h, 70%;
b) Pd/C, H$_2$, CH$_3$COOC$_2$H$_5$, 3 atm, 2 h, 100%;
c) p-toluenesulphonic acid, toluene, MeOH, reflux, 24 h, 95%;
d) CH$_3$COCl, AlCl$_3$, ClCH$_2$CH$_2$Cl, 0° C., 100%;
e) KClO, KOH, K$_2$CO$_3$, MeOH, H$_2$O, 0° C. to room temperature 1 h then reflux 1 h, 90%;
f) (1) SOCl$_2$, CH$_2$Cl$_2$, reflux (50° C.), 6 h; (2) 3-Flouroaniline, THF, DIEA, reflux, 0.5 h, 90%;
g) AlCl$_3$, CH$_3$CH$_2$SH, CH$_2$Cl$_2$, 0° C. to room temperature 2 h, 92%;
h) BrCH$_2$COOCH$_3$, K$_2$CO$_3$, THF, reflux, 1 h, 98%;
i) LiOH, MeOH, H$_2$O, reflux, 1 h, 100%;
j) PyBOP, R$_4$NH$_2$, DIEA, DMF, 0° C. to room temperature, 2 h, 90~95%.

Preparation of Tricyclo[6.2.2.0$^{2,7}$]dodecane-4,9-diene-3,6-dione (Compound 51)

1,3-Cyclohexadiene (0.8 g, 0.1 mol) was added to a suspension of YbCl$_3$ (2.80 g, 10 mmol) in 50 ml CH$_2$Cl$_2$ dropwise at room temperature. The mixture was stirred for 5 h and diluted with 200 ml CH$_2$Cl$_2$ and washed with water and brine. The organic layer was dried over anhydrous Na$_2$SO$_4$ and the solvent was removed to give the crude product. Recrystallization from hexane provided 13.2 g (70%) of 51 as yellow needle. mp 93-94° C. $^1$HNMR (300 M, CDCl$_3$) δ 1.37 (m, 2H), 1.70 (m, 2H), 2.99 (bs, 2H), 3.22 (bs, 2H), 6.22 (m, 2H), 6.65 (s, 2H). MS (EI) m/z: 188(M$^+$).

Preparation of Tricyclo[6.2.2.0$^{2,7}$]dodecane-3,6-dione (Compound 52)

10% palladium on carbon catalyst 0.1 g was added to a solution of 51 (9.4 g, 50 mmol) in ethyl acetate (50 ml). The mixture was shaken for 2 h under 3 atm of hydrogen gas on a Parr hydrogenator and then filtered to remove the catalyst. The solvent was removed under reduced pressure and the crude product was obtained. Recrystallization from methanol gave 10.1 g (100%) of pure 52. $^1$HNMR (300 M, CDCl$_3$) δ 1.43 (m, 4H), 1.60 (m, 4H), 2.68 (bs, 2H), 2.63 (m, 2H), 2.85 (m, 4H). $^{13}$CNMR (300 M, CDCl$_3$) 22, 25, 27, 38, 50, 210. MS (EI) m/z: 192(M$^+$).

Preparation of 3-Ethoxy Tricyclo[6.2.2.0$^{2,7}$]dodeca-2,4,6-triene (Compound 53)

A mixture of diketone 52 (5.76 g, 30 mmol), ethanol (100 ml), p-toluenesulphonic acid (0.95 g, 5 mmol), and toluene (200 ml) was heated to reflux overnight under a soxhlet extractor filled with anhydrous Mg$_2$SO$_4$. K$_2$CO$_3$ (1.5 g) was added and heating was continued for an additional 15 min. The cooled solution was washed by a K$_2$CO$_3$ solution and brine, dried over Na$_2$SO$_4$, and the solvent was removed to give the crude product. The product was purified by column chromatography to afford 5.96 g (95%) of 53. $^1$HNMR (300 M, CDCl$_3$) δ 1.34~1.43 (m, 7H), 1.74 (m, 4H), 2.96 (bs, 1H), 3.50 (m, 1H), 4.03 (m, 2H), 6.77 (m, 2H), 7.10 (m, 1H). $^{13}$CNMR (300 M, CDCl$_3$) 15, 25, 26, 34, 64, 109, 116, 126, 132, 146, 153. HR-MS (EI) m/z: 202.1353 (M$^+$, requires 202.1352).

Preparation of 1-(6-Ethoxy-tricyclo[6.2.2.0$^{2,7}$]dodeca-2,4,6-triene-3-yl)-ethanone (Compound 54)

The preparation of 54 was based on a procedure similar to that described in Scheme 2 for the conversion of 40 to 41 (yield 100%). $^1$HNMR (300 M, CDCl$_3$) δ 1.30 (m, 4H), 1.44 (t, 3H), 1.74 (m, 4H), 2.56 (s, 3H), 3.56 (bs, 1H), 4.10 (m, 3H), 6.73 (d, 1H), 7.60 (d, 1H). The structure assignment of 54 was determined by ID NOE. Irradiate δ 2.56 (COCH$_3$), NOE of δ 7.60 (aromatic) and 4.12 (bs, phCH) were observed. Irradiate δ 6.73 (aromatic), NOE of 4.10 (q, OCH$_2$CH$_3$) and 7.60 (aromatic) were observed. $^{13}$CNMR (300 M, CDCl$_3$) 15, 25, 29, 64, 108, 127, 128, 133, 147, 156, 200. MS (EI) m/z: 244.

Preparation of 6-Ethoxy-tricyclo[6.2.2.0$^{2,7}$]dodeca-2,4,6-triene-3-carboxylic Acid (Compound 55)

The preparation of 55 was based on a procedure similar to that described in Scheme 2 for the conversion of 41 to 42 (yield 90%). $^1$HNMR (400 M, DMSO-D$_6$) δ 1.20 (m, 4H), 1.33 (t, 3H), 1.70 (m, 4H), 3.45 (bs, 1H), 4.07 (m, 2H), 4.22 (bs, 1H), 6.85 (d, 1H), 7.69 (d, 1H). $^{13}$CNMR (300 M, DMSO-D$_6$) 15, 25, 29, 63, 108, 118, 129, 131, 147, 155, 168. MS (EI) m/z: 246.

Preparation of 6-Ethoxy-tricyclo[6.2.2.0$^{2,7}$]dodeca-2,4,6-triene-3-carboxylic Acid (3-fluoro-phenyl)-amide (Compound 56)

The preparation of 56 was based on a procedure similar to that described in Scheme 2 for the conversion of 42 to 43 (yield 90%). $^1$HNMR (300 M, DMSO-D$_6$) δ 1.16~1.37 (m, 7H), 1.71 (m, 4H), 3.46~3.50 (bs, 2H), 4.08 (m, 2H), 6.89 (m, 2H), 7.34 (m, 2H), 7.47 (m, 1H), 7.71 (d, 1H), 10.37 (s, 1H). MS (EI) m/z: 339.

Preparation of 6-Hydroxy-tricyclo[6.2.2.0$^{2,7}$]dodeca-2,4,6-triene-3-carboxylic Acid (3-fluoro-phenyl)-amide (Compound 57)

The preparation of 57 was based on a procedure similar to that described in Scheme 2 for the conversion of 43 to 44 (yield 92%). $^1$HNMR (300 M, DMSO-D$_6$) δ 1.23 (m, 4H), 1.70 (m, 4H), 3.42 (bs, 1H), 3.50 (bs, 1H), 6.72 (d, 1H), 6.87 (m, 1H), 7.21 (d, 1H), 7.34 (m, 1H), 7.46 (m, 1H), 7.71 (d, 1H), 9.63 (s, 1H), 10.37 (s, 1H). MS (EI) m/z: 311.

Preparation of [6-(3-Fluoro-phenylcarbamoyl)-tricyclo[6.2.2.0$^{2,7}$]dodeca-2,4,6-triene-3-yloxy]-acetic Acid Methyl Ester (Compound 58)

The preparation of 58 was based on a procedure similar to that described in Scheme 2 for the conversion of 44 to 45 (yield 98%). $^1$HNMR (300 M, DMSO-D$_6$) δ 1.25 (m, 4H), 1.73 (m, 4H), 3.48~3.50 (bs, 2H), 4.88 (s, 2H), 6.83~6.92 (m, 2H), 7.30~7.38 (m, 2H), 7.46 (m, 1H), 7.71 (d, 1H), 10.41 (s, 1H). MS (EI) m/z: 383.

Preparation of [6-(3-Fluoro-phenylcarbamoyl)-tricyclo[6.2.2.0$^{2,7}$]dodeca-2,4,6-triene-3-yloxy]-acetic Acid (Compound 59)

The preparation of 59 was based on a procedure similar to that described in Scheme 2 for the conversion of 45 to 46 (yield 100%). $^1$HNMR (300 M, DMSO-D$_6$) δ 1.25 (m, 4H), 1.73 (m, 4H), 3.48~3.52 (bs, 2H), 4.74 (s, 2H), 6.79~6.92 (m, 2H), 7.32~7.38 (m, 2H), 7.46 (m, 1H), 7.71 (d, 1H), 10.40 (s, 1H). $^{13}$CNMR (300 M, CDCl$_3$) 25, 29, 64, 105, 108, 109, 115, 125, 130, 132, 141, 144, 153, 162, 167, 170. MS (EI) m/z: 369.

Preparation of [6-Cyclopropylcarbamoylmethoxy-tricyclo[6.2.2.0$^{2,7}$]dodeca-2,4,6-triene-3-carboxylic Acid (3-fluoro-phenyl)-amide (Compound 61)

The preparation of 61 was based on the general procedure for amide coupling described above in Example 2. $^1$HNMR (300 M, DMSO-D$_6$) δ 0.48 (m, 2H), 0.64 (m, 2H), 1.28 (m, 4H), 1.74 (m, 4H), 2.68 (m, 1H), 3.50 (bs, 1H), 3.57 (bs, 1H), 4.52 (s, 2H), 6.79 (m, 1H), 6.90 (m, 1H), 7.36 (m, 2H), 7.48 (m, 1H), 7.54 (d, 1H), 8.15 (d, 1H), 10.42 (s, 1H).

Preparation of 6-[(4-Hydroxy-Phenylcarbamoyl)-methoxy-tricyclo[6.2.2.0$^{2,7}$]dodeca-2,4,6-triene-3-carboxylic Acid (3-fluoro-phenyl)-amide (Compound 62)

The preparation of 62 was based on the general procedure for amide coupling described above in Example 2. $^1$HNMR (300 M, DMSO-D$_6$) δ 1.27 (m, 4H), 1.74 (m, 4H), 3.49 (bs, 1H), 3.60 (bs, 1H), 4.73 (s, 2H), 6.68 (m, 2H), 6.90 (m, 2H), 7.34~7.58 (m, 5H), 7.73 (d, 1H), 9.23 (bs, 1H), 9.88 (s, 1H), 10.39 (s, 1H).

Preparation of 6-[(2,2,2-Trifluoro-ethylcarbamoyl)-methoxy]-tricyclo[6.2.2.0$^{2,7}$]dodeca-2,4,6-triene-3-carboxylic Acid (3-fluoro-phenyl)-amide (Compound 63)

The preparation of 63 was based on the general procedure for amide coupling described above in Example 2. $^1$HNMR (300 M, DMSO-D$_6$) δ 1.26 (m, 4H), 1.73 (m, 4H), 3.49 (bs, 1H), 3.60 (bs, 1H), 3.98 (m, 2H), 4.66 (s, 2H), 6.79~6.91 (m, 2H), 7.30~7.48 (m, 3H), 7.71 (d, 1H), 8.70 (t, 1H), 10.40 (s, 1H).

Table 3 below shows the HOXA1/PBX1/DNA antagonist activities of several 3,6-disubstituted tricyclo[6.2.2.0$^{2,7}$]dodeca-2(7),3,5-triene derivatives, compounds 61, 62, and 63 in particular.

TABLE 3

HOXA1/PBX1/DNA Antagonist Activity of
3,6-Disubstituted tricyclo [6.2.2.0$^{2,7}$]dodeca-2(7),3,5-trienes

| Compound | R$_4$ | HOXA1/PBX1 IC$_{50}$ (µM)$^a$ |
|---|---|---|
| 61 | cyclopropyl | 562 |
| 62 | 4-hydroxyphenyl | 196 |
| 63 | 2,2,2-trifluoroethyl | 258 |

Example 4

Synthesis of 5,8-Disubstituted 1,2,3,4-tetrahydro-1,4-methano-naphthalene Derivatives Scheme 4 below shows a method of synthesizing 5,8-disubstituted 1,2,3,4-tetrahydro-1,4-methano-naphthalene derivatives 73, based on the same reaction scheme as Scheme 3 described above that converted 51 to 60.

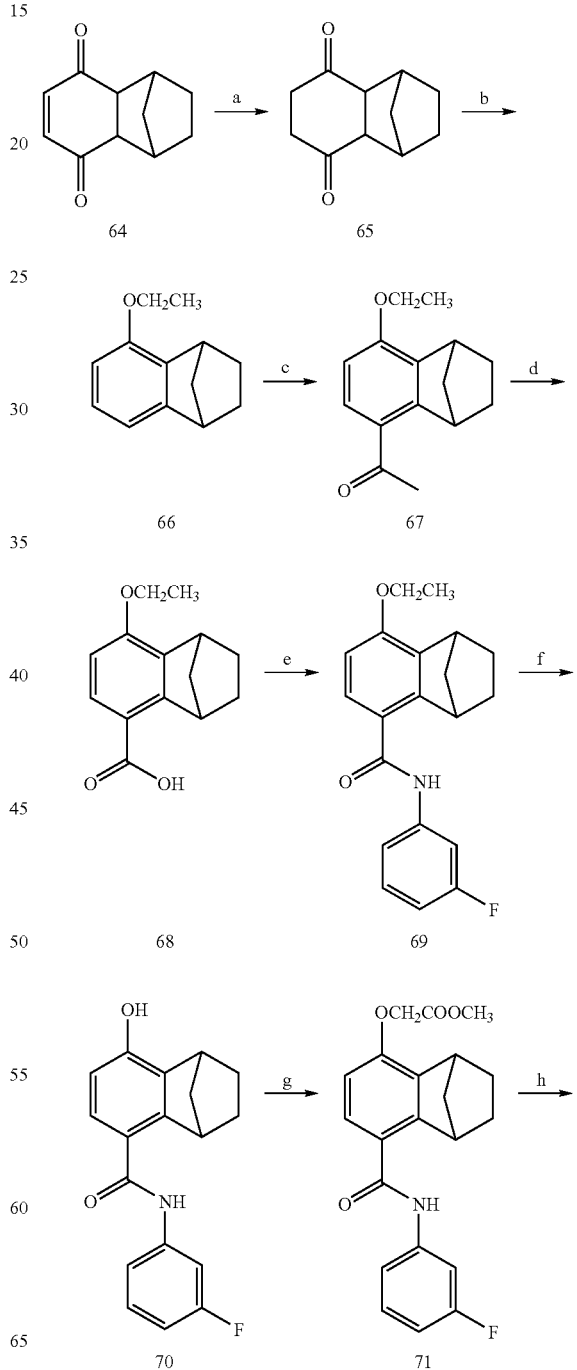

Scheme 4

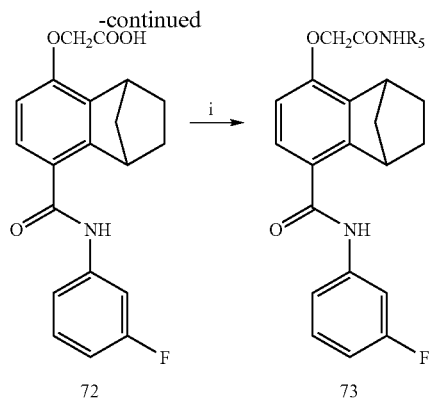

a) Pd/C, H$_2$, CH$_3$COOC$_2$H$_5$, 3 atm, 2 h;
b) p-toluenesulphonic acid, toluene, MeOH, reflux, 24 h;
c) CH$_3$COCl, AlCl$_3$, ClCH$_2$CH$_2$Cl, 0° C.;
d) KClO, KOH, K$_2$CO$_3$, MeOH, H$_2$O, 0° C. to room temperature 1 h then reflux 1 h;
e) (1) SOCl$_2$, CH$_2$Cl$_2$, reflux (50° C.), 6 h; (2) 3-Flouroaniline, THF, DIEA, reflux, 0.5 h;
f) AlCl$_3$, CH$_2$CH$_2$SH, CH$_2$Cl$_2$, 0° C. to room temperature 2 h;
g) BrCH$_2$COOCH$_3$, K$_2$CO$_3$, THF, reflux, 1 h;
h) LiOH, MeOH, H$_2$O, reflux 1 h;
i) PyBOP, R$_4$NH$_2$, DIEA, DMF, 0° C. to room temperature, 2 h.

Although the invention has been described in detail, for the purpose of illustration, it is understood that such detail is for that purpose and variations can be made therein by those skilled in the art without departing from the spirit and scope of the invention which is defined by the following claims.

---

What is claimed is:

1. A compound having the following formula:

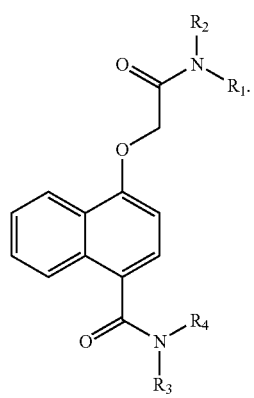

Formula I wherein:
  $R_1$-$R_2$ are individually selected from the group consisting of: H, $C_1$-$C_{12}$ alkyl, heteroatom and multiple heteroatom substituted $C_1$-$C_{12}$ alkyl, $C_1$-$C_{12}$ branched or cyclic alkyl, aryl and substituted aryl, heteroaryl and substituted heteroaryl, substituted alkylaryl, amines, $CH_2COOCH_2CH_3$, $CH_2COOH$, and $CH_2C\equiv C$, wherein the substitution in any of the substituted groups comprises substituents selected from the group consisting of hydrogen, halogen, oxygen, OH, $OCH_3$, and methyl;
  $R_3$ is H; and
  $R_4$ is 3-fluorophenyl.

2. The compound according to claim 1, wherein the compound has the following structure:

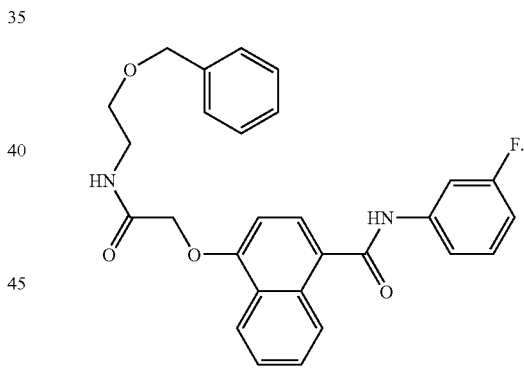

3. The compound according to claim 1, wherein the compound has the following structure:

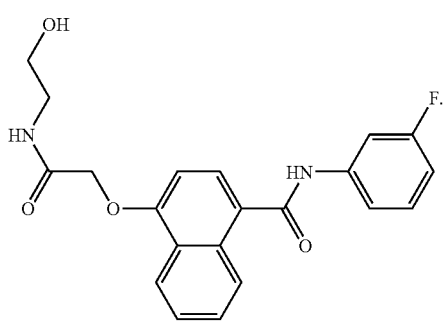

4. The compound according to claim 1, wherein the compound has the following structure:

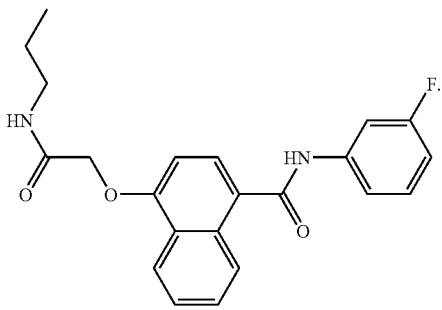

5. The compound according to claim 1, wherein the compound has the following structure:

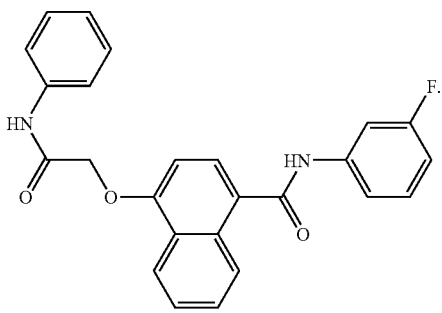

6. The compound according to claim 1, wherein the compound has the following structure:

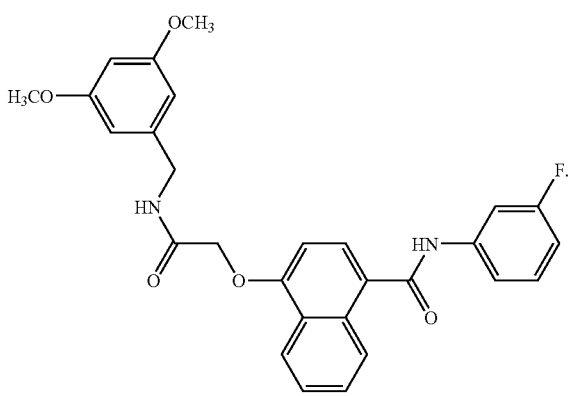

7. The compound according to claim 1, wherein the compound has the following structure:

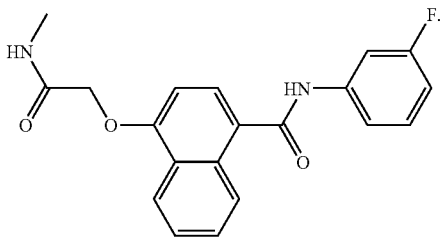

8. The compound according to claim 1, wherein the compound has the following structure:

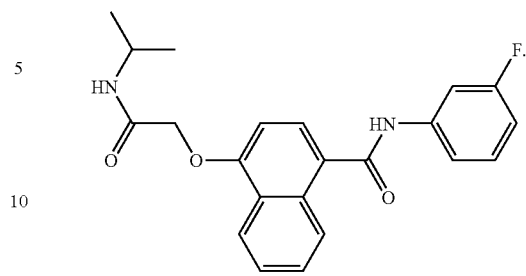

9. The compound according to claim 1, wherein the compound has the following structure:

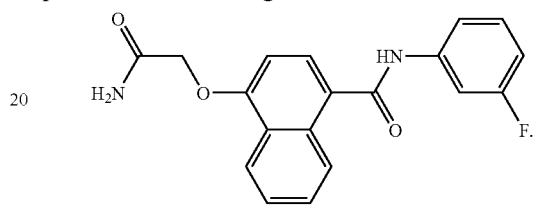

10. The compound according to claim 1, wherein the compound has the following structure:

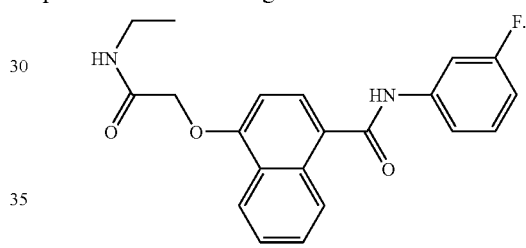

11. The compound according to claim 1, wherein the compound has the following structure:

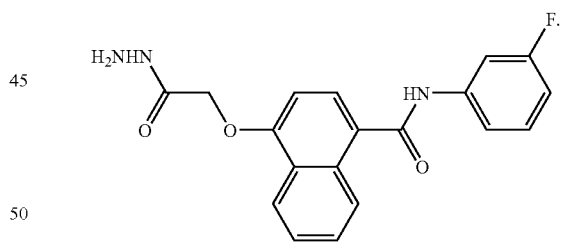

12. The compound according to claim 1, wherein the compound has the following structure:

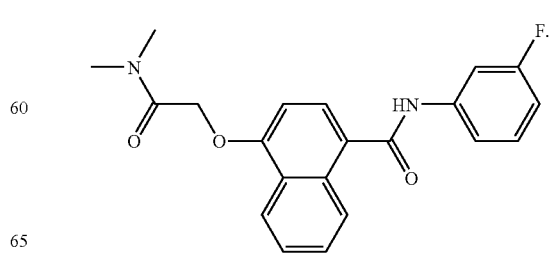

13. The compound according to claim 1, wherein the compound has the following structure:

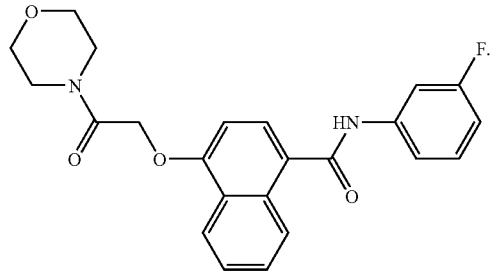

14. The compound according to claim 1, wherein the compound has the following structure:

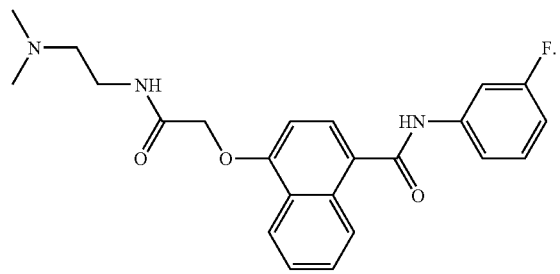

15. The compound according to claim 1, wherein the compound has the following structure:

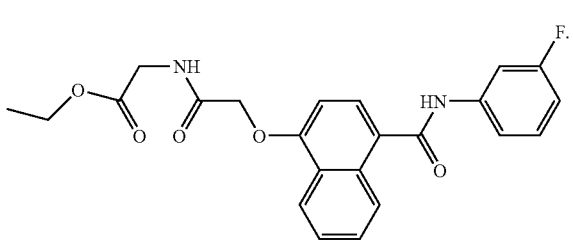

16. The compound according to claim 1, wherein the compound has the following structure:

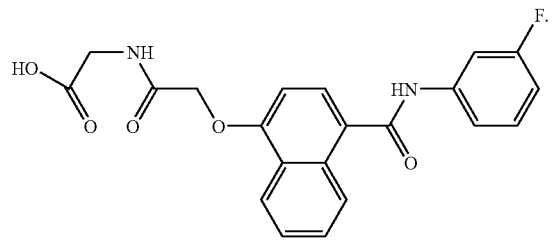

17. The compound according to claim 1, wherein the compound has the following structure:

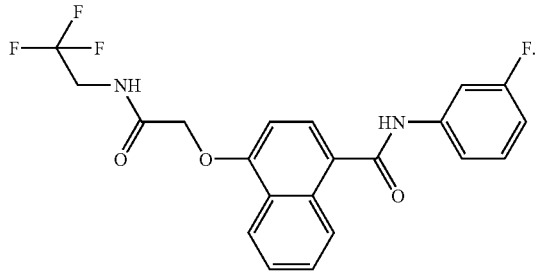

18. The compound according to claim 1, wherein the compound has the following structure:

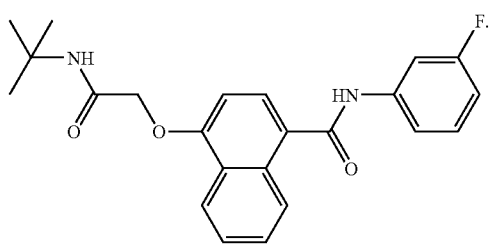

19. The compound according to claim 1, wherein the compound has the following structure:

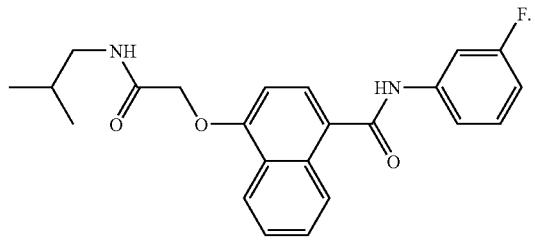

20. The compound according to claim 1, wherein the compound has the following structure:

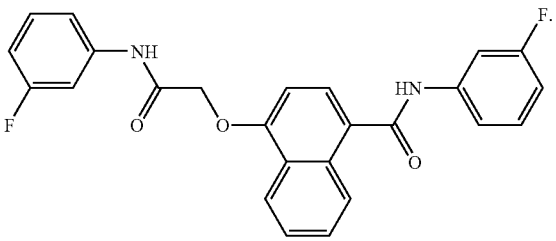

21. The compound according to claim 1, wherein the compound has the following structure:

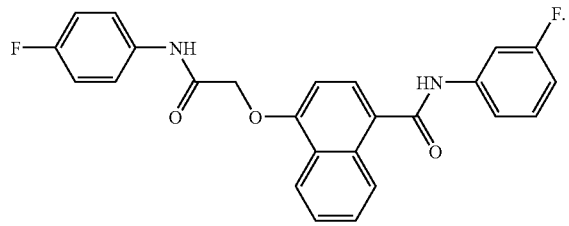

22. The compound according to claim 1, wherein the compound has the following structure:

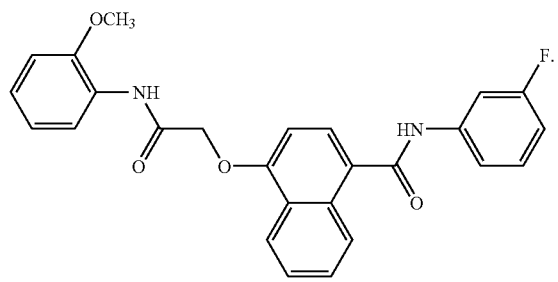

23. The compound according to claim 1, wherein the compound has the following structure:

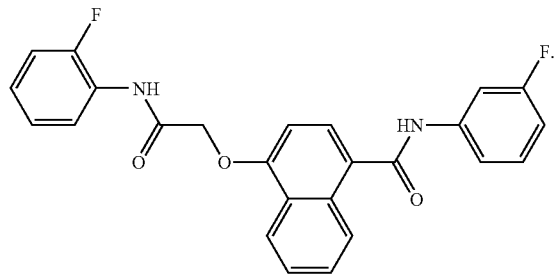

24. The compound according to claim 1, wherein the compound has the following structure:

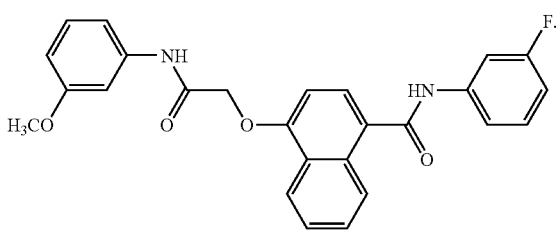

25. The compound according to claim 1, wherein the compound has the following structure:

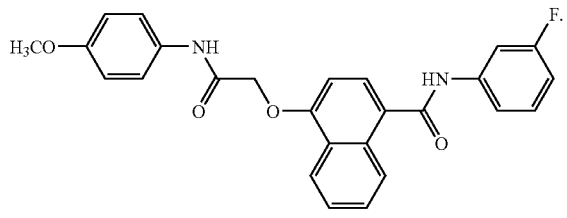

26. The compound according to claim 1, wherein the compound has the following structure:

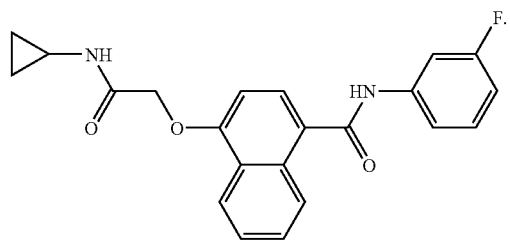

27. The compound according to claim 1, wherein the compound has the following structure:

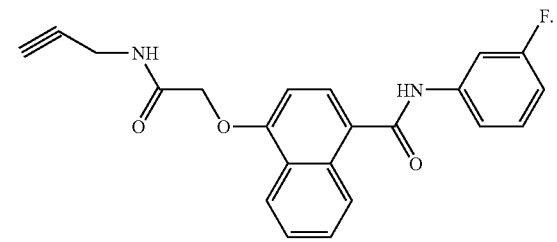

28. The compound according to claim 1, wherein the compound has the following structure:

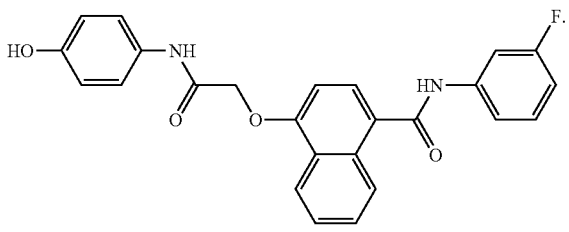

29. The compound according to claim 1, wherein the compound has the following structure:

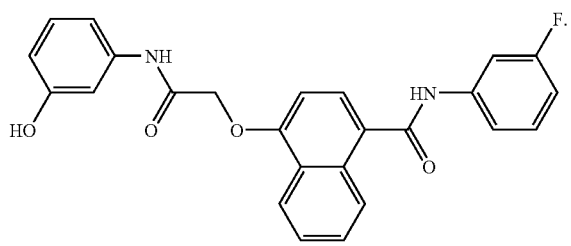

30. The compound according to claim 1, wherein the compound has the following structure:

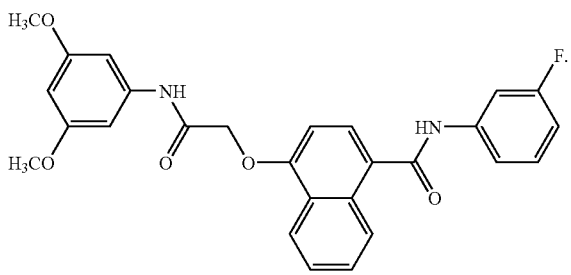

31. The compound according to claim 1, wherein the compound has the following structure:

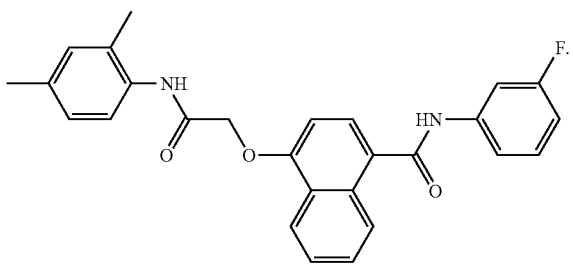

32. The compound according to claim 1, wherein the compound has the following structure:

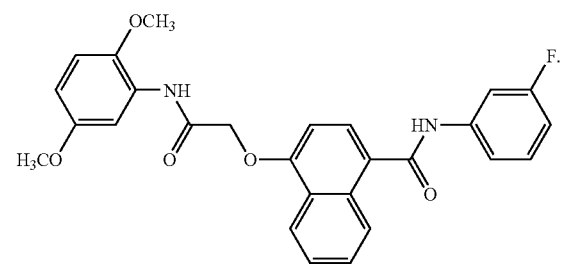

33. The compound according to claim 1, wherein the compound has the following structure:

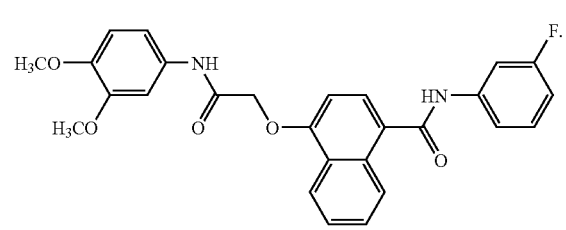

34. The compound according to claim 1, wherein the compound has the following structure:

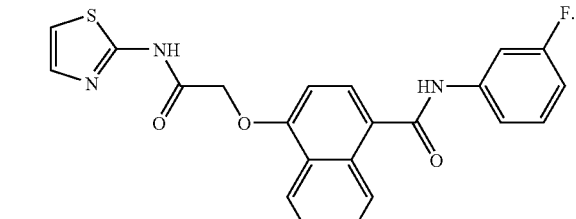

35. The compound according to claim 1, wherein the compound has the following structure:

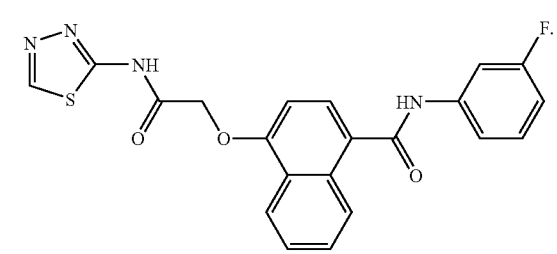

36. The compound according to claim 1, wherein the compound has the following structure:

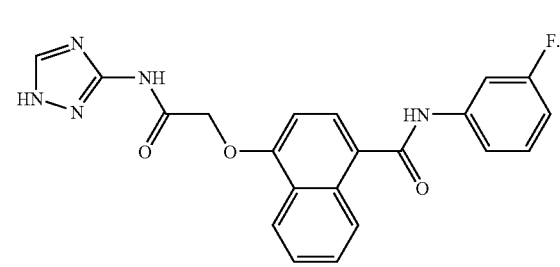

37. The compound according to claim 1, wherein the compound has the following structure:

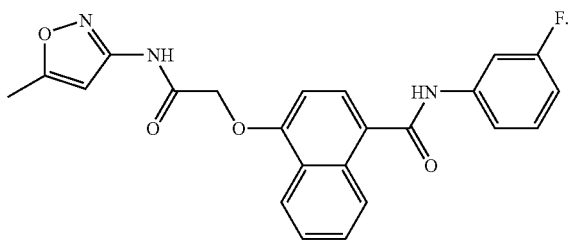

38. The compound according to claim 1, wherein the compound has the following structure:

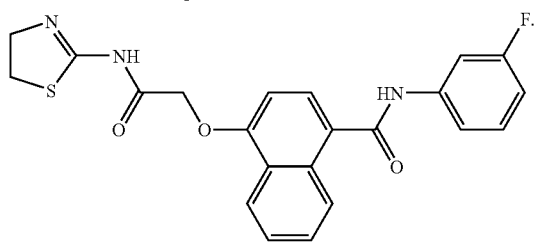

39. A compound having the following formula:

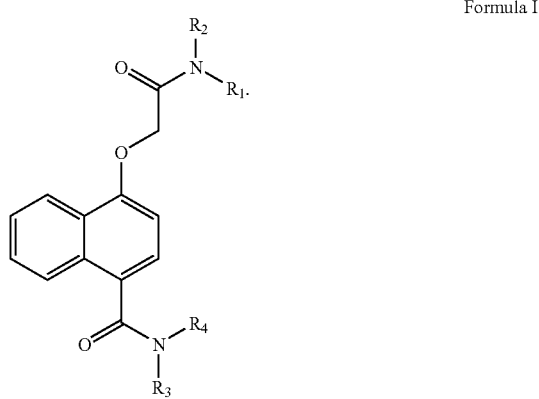

Formula I wherein:

$R_1$ is selected from the group consisting of H, $C_1$-$C_{12}$ alkyl, substituted $C_1$-$C_{12}$ alkyl, $C_3$-$C_{12}$ branched or cyclic alkyl, aryl and substituted aryl, heteroaryl and substituted heteroaryl, substituted alkylaryl, amines, $CH_2COOCH_2CH_3$, $CH_2COOH$, and $CH_2C\equiv C$, wherein the substitution in any of the substituted groups comprises substituents selected from the group consisting of hydrogen, halogen, oxygen, OH, $OCH_3$, and methyl;

$R_2$ is H or methyl;

$R_3$ is H; and $R_4$ is 3-fluorophenyl.

40. The compound according to claim 39, wherein $R_2$ is H.

41. The compound according to claim 39, wherein $R_1$ is selected from the group consisting of H, $C_1$-$C_4$ alkyl, substituted $C_1$-$C_4$ alkyl, $C_3$-$C_4$ branched or cyclic alkyl, aryl and substituted aryl, heteroaryl and substituted heteroaryl, and $CH_2C\equiv C$, wherein the substitution in any of the substituted groups comprises substituents selected from the group consisting of hydrogen, halogen, OH, and $OCH_3$.

42. The compound according to claim 39, wherein $R_1$ is selected from the group consisting of H, $C_1$-$C_4$ alkyl, $C_3$-$C_4$ branched or cyclic alkyl, phenyl, benzyl, thiazole, thiadiazole, triazole, isoxazole, amines, $CH_2COOCH_2CH_3$, $CH_2COOH$, and $CH_2C\equiv C$, wherein $C_1$-$C_4$ alkyl, phenyl, benzyl, thiazole, thiadiazole, triazole, and isoxazole are optionally substituted with substituents selected from the group consisting of hydrogen, halogen, methyl, OH, and $OCH_3$.

43. The compound according to claim 42, wherein $R_1$ is selected from the group consisting of H, $C_1$-$C_4$ alkyl, $C_3$-$C_4$ branched or cyclic alkyl, phenyl, benzyl, thiazole, thiadiazole, triazole, isoxazole, and $CH_2C\equiv C$, wherein $C_1$-$C_4$ alkyl, phenyl, benzyl, thiazole, thiadiazole, triazole, and isoxazole are optionally substituted with substituents selected from the group consisting of hydrogen, halogen, methyl, OH, and $OCH_3$.

* * * * *

UNITED STATES PATENT AND TRADEMARK OFFICE
CERTIFICATE OF CORRECTION

PATENT NO. : 7,662,750 B2 Page 1 of 1
APPLICATION NO. : 11/005194
DATED : February 16, 2010
INVENTOR(S) : Hangauer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1318 days.

Signed and Sealed this

Thirtieth Day of November, 2010

David J. Kappos
*Director of the United States Patent and Trademark Office*

SEQUENCE LISTING

<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:
      Pentapeptide sequence of HOXB1 protein

<400> SEQUENCE: 1

Phe Asp Trp Met Lys
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:  Highly
      conserved pentapeptide region of the HOX family of
      peptide domains
<220> FEATURE:
<221> NAME/KEY: VARIANT
<222> LOCATION: (1)
<223> OTHER INFORMATION: X at position 1 is either F or Y
<220> FEATURE:
<221> NAME/KEY: VARIANT
<222> LOCATION: (2)
<223> OTHER INFORMATION: X at position 2 is either P or D
<220> FEATURE:
<221> NAME/KEY: VARIANT
<222> LOCATION: (5)
<223> OTHER INFORMATION: X at position 5 is either K or R

<400> SEQUENCE: 2

Xaa Xaa Trp Met Xaa
 1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence:  Sequence
      of the wild-type HOX-A5 peptide (residues 173 to 184)

<400> SEQUENCE: 3

```
Gln Pro Gln Ile Tyr Pro Trp Met Arg Lys Leu His
  1               5                  10

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 4
ctctcctttt gattgattaa                                              20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 5
agagcttaat caatcaaaag g                                            21
```